(12) United States Patent
Pasek et al.

(10) Patent No.: US 7,273,944 B2
(45) Date of Patent: Sep. 25, 2007

(54) METHODS FOR PRODUCING COPPER ETHANOLAMINE SOLUTIONS

(75) Inventors: Eugene A. Pasek, Ravenna, OH (US); Jayesh P. Patel, Stone Mtn., GA (US); Susan M. Thomason, Loganville, GA (US); Eric W. Lummus, Stockbridge, GA (US); Kenneth E. Cogan, Dunwoody, GA (US)

(73) Assignee: Arch Chemicals, Inc., Norwalk, CT (US)

( * ) Notice: Subject to any disclaimer, the term of this patent is extended or adjusted under 35 U.S.C. 154(b) by 0 days.

(21) Appl. No.: 10/917,598

(22) Filed: Aug. 13, 2004

(65) Prior Publication Data

US 2005/0171369 A1    Aug. 4, 2005

Related U.S. Application Data

(60) Provisional application No. 60/524,112, filed on Nov. 19, 2003.

(51) Int. Cl.
C07F 1/08    (2006.01)
(52) U.S. Cl. ..................................... 556/113; 556/110
(58) Field of Classification Search .................. None
See application file for complete search history.

(56) References Cited

U.S. PATENT DOCUMENTS

| | | | |
|---|---|---|---|
| 3,760,070 | A | 9/1973 | Joice et al. |
| 4,624,839 | A | 11/1986 | Wolcott et al. |
| 4,714,597 | A | 12/1987 | Treviñño |
| 4,808,407 | A | 2/1989 | Hein et al. |
| 4,929,454 | A | 5/1990 | Findlay et al. |
| 4,944,935 | A | 7/1990 | Langner et al. |
| 5,084,201 | A | 1/1992 | Greco |
| 5,304,666 | A | 4/1994 | McLain |
| 5,409,567 | A | 4/1995 | Lytle et al. |
| 5,492,681 | A | 2/1996 | Pasek et al. |
| 5,634,967 | A | 6/1997 | Williams et al. |
| 5,635,217 | A | 6/1997 | Goettsche et al. |
| 5,853,766 | A | 12/1998 | Goettsche et al. |
| 6,123,088 | A | 9/2000 | Ho |
| 6,229,045 | B1 | 5/2001 | Ringer et al. |
| 6,294,071 | B1 | 9/2001 | Miller et al. |
| 6,352,583 | B1 | 3/2002 | Goettsche et al. |
| 6,441,016 | B2 | 8/2002 | Goettsche et al. |
| 6,447,563 | B1 | 9/2002 | Mahulikar |
| 6,646,147 | B2 | 11/2003 | Richardson et al. |
| 6,905,531 | B2 | 6/2005 | Richardson et al. |
| 6,905,532 | B2 | 6/2005 | Richardson et al. |
| 2001/0006684 | A1 | 7/2001 | Goettsche et al. |
| 2003/0162986 | A1 | 8/2003 | Richardson |
| 2004/0191143 | A1 | 9/2004 | Richardson et al. |
| 2005/0130866 | A1 | 6/2005 | Richardson et al. |

FOREIGN PATENT DOCUMENTS

| | | |
|---|---|---|
| CA | 2262186 | 9/1999 |
| DE | 3447027 A1 | 7/1986 |
| DE | 4112652 A1 | 10/1992 |
| EP | 0211181 B1 | 9/1989 |
| WO | WO91/01942 A1 | 2/1991 |
| WO | WO 01/51683 A1 | 7/2001 |
| WO | WO 03/069025 A2 | 8/2003 |
| WO | WO 03/069025 A3 | 8/2003 |

OTHER PUBLICATIONS

Anonymous (Phillips Petroleum Co., Titanium Ltd.), "Preventing corrosion in baffle heat exchange bundles," *Anti-Corrosion Methods and Materials*, 38(7):17 (Jul. 1991).

Anonymous, "Appendix 4B Test Chemistry," from an application for a Utah chemical environmental state permit "MMD-1, RD&D", published Dec. 15, 1998 at www.eq.state.ut.us/EQSHW/CDS/MMD_Permit/ATCH04ApendB.pdf.

Anonymous, "Methylamines storage and handling," Air Porducts brochure (copyright 1996) posted at www.airproducts.com/Products/Chemicals/Amines/Newsstand/StorageandHandlingInformation.htm.

Blachly, C.H.; and Ravner, H., "Studies of submarine carbon dioxide scrubber operation: effect of an additive package for the stabilization of monoethanolamine solutions," Naval Research Laboratory Memorandum Report No. 1598, US Department of Commerce, National Technical Information Service, document No. AD 461151 (US Department of Commerce), Mar. 1965.

Blachly, C.H.; and Ravner, H., "The stabilization of monoethanolamine solutions for submarine carbon dioxide scrubbers," Naval Research Laboratory Report No. 6189, National Technical Information Service, document No. AD 609888 (US Department of Commerce), Dec. 4, 1964.

Blachly, C.H.; and Ravner, H., "The stabilization of monoethanolamine (MEA) solutions in carbon dioxide scrubbers," *Chem. Abstr.* AN65:3425; DN 1203710; abstract of *149th Am. Chem. Soc. Meeting* (Detroit, Apr. 4-9, 1965), Am. Chem. Soc. Div. Petrol. Chem. Inc., Preprints, 10(2):D145-D155 (Apr. 1965).

(Continued)

*Primary Examiner*—Brian Davis
(74) *Attorney, Agent, or Firm*—Dale L. Carlson; Wiggin and Dana LLP

(57) ABSTRACT

Provided are preservation formulations and methods, e.g., formulations for the preservation of wood. In particular, provided are methods for the production of copper mono-ethanolamine aqueous solutions from metallic copper and monoethanolamine.

16 Claims, 11 Drawing Sheets

OTHER PUBLICATIONS

Browning, G.J., and Weiland, R.H., "Physical solubility of carbon dioxide in aqueous alkanolamines via nitrous oxide analogy," *J. Chem. Eng. Data*, 39:817-822 (1994).

Button, J.K., and Gubbins, K.E., "SAFT prediction of vapour-liquid equilibria of mixtures containing carbon dioxide and aqueous monoethanolamine or diethanolamine," *Fluid Phase Equilibria*, 158-160:175-181 (1999).

Dawodu, O.F., and Meisen, A., "Solubility of carbon dioxide in aqueous mixtures of alkanolamines," *J. Chem. Eng. Data*, 39:548-552 (1994).

DuPart, M.S.; Bacon, T.R.; and Edwards, D.J., et al., "Understanding corrosion in alkanolamine gas treating plants," *Hydrocarbon Processing*, Apr. 1993:75-80 (Part I) and May 1993:89-94 (Part II).

Inoue, Yoshio; Ohno, Shigeru; and Hashimoto, Harukichi, "Reaction of carbon dioxide with copper (II) complexes bearing O,N-chelate ligand. A reversible insertion," *Technology Reports, Tohoku Univ.*, 48(1):1-5 (1983).

Jou, F.-Y.; Mather, A.E.; and Otto, F.D., "The solubility of $CO_2$ in a 30 mass percent monoethanolamine solution," *The Canadian Journal of Chemical Engineering*, 73:140-147 (Feb. 1995).

Khitrin, S.V.; Fuks, S.L.; and Devyaterikova, S.V., "Properties and composition of the wastes of monoethanolamine treatment of hydrogen to remove carbon dioxide," *Russian Journal of Applied Chemistry*, 75(1):63-67 (2002).

Kosseim, A.J.; McCullough, J.G.; and Coarsey, C.L., "New gas-sweetening system is energy saver," *Oil & Gas Journal*, 82(12):174-178 (1984).

Kostić, S., and Mladenović, S., "Korozija čelika A-53 i bakra u vodenom rastvoru monoetanolamina," ["Corrosion of A-53 steel and copper in an aqueous solution of monoethanolamine"], *Zastita Materijala*, 21(7-8):167-170 (1973). Abstract in English at p. 170; also *Chem. Abstr.*, AN 1974:66042, DN 80:66042 (1974).

Montrone, E.D., and Long, W.P., "Choosing materials for $CO_2$ absorption systems," *Chemical Engineering*, 78(2):94, 96, 98-99 (Jan. 25, 1971).

Neimark, I.E., et al., "Synthesis of specific silica gels by a modification of their surface," *Chem. Abstr.* 54:115168 (1960), abstract of *Doklady Adademii Nauk SSSR*, 132:1356-1359 (1960).

Park, S.H., et al., "Correlation and prediction of the solubility of carbon dioxide in aqueous alkanolamine and mixed alkanolamine solutions," *Ind. Eng. Chem. Res.*, 41:1658-1665 (2002).

Raudsepp, Kh.T.; Aarna, A. Ya., "Purification of gases obtained from Estonian bituminous schist," *Chem. Abstr.* 54:121762 (1960), abstract of *Trudy Tallin. Politekh. Inst., Ser. A*, (73):160-178 (1956).

Ryazanov, I.P., "The separation of lead and cadmium copper with monoethanolamine carbonate," *Chem. Abstr.*, 54:27502 (1960), abstract of *Sbornik Nauch. Trudov Magnitogorstk. Gorno-Met. Inst.* 1957(13):22-28 (1957).

Sample, J.L., "Amine inhibiting . . . how good is it?" *Chem. Abstr.* AN 84:4528, DN 3204623, abstract of *Gas Process. Assoc. Annu. Meet.* [Houston, Mar. 18-20, 1985; paper (adapted) in *Hydrocarbon Process. Int. Ed.* 64(5):72-73 (May 1985)].

Shneerson, A.L., Le Bush, A.G., "Absorption of carbon dioxide by ethanolamines. I. Rate of absorption of carbon dioxide in solutions of mono-, di-, and triethanolamine," *Chem. Abstr.* 41:21681 (1947), abstract of *Zhurnal Prikladnoi Khimii*, 19:869-880 (1946).

Strazisar, B.R., Anderson, R.R.; and White, C.M., "Degradation pathways for monoethanolamine in a $CO_2$ capture facility," *Energy & Fuels*, 17:1034-1039 (2003).

Yao, Fuqi, "Qualitative identification of metallic copper," *Chem. Abstr* AN 1992:523591, DN 117:123591, abstract of *Huaxue Shijie*, 33(2):76-77 (1992).

International Preliminary Report on Patentability for corresponding International Patent Application No. PCT/US04/39069, (2005).

300 GALLON REACTOR LAYOUT CIRCULATION DESIGN

METHODS FOR PRODUCING COPPER ETHANOLAMINE SOLUTIONS

CROSS REFERENCE TO RELATED APPLICATIONS

This application claims priority to U.S. Provisional Application No. 60/524,112, filed Nov. 19, 2003, the disclosure of which is incorporated herein by reference.

TECHNICAL FIELD

This application is in the field of preservation formulations and methods, e.g., formulations for the preservation of wood. This application particularly provides methods for the production of copper ethanolamine aqueous solutions from metallic copper and ethanolamine.

BACKGROUND OF THE INVENTION

Preservatives are very common in commercial and industrial products. The need for effective and economical preservative compositions is well known. There are a wide variety of applications where inhibiting the growth of microorganisms is necessary, as for example personal care products such as shampoos, conditioners, hair care products, creams, lotions, cosmetics, soap, skin care products; household products such as laundry detergents, hard surface cleaners, and fabric softeners; and industrial products and materials, such as adhesives, sizes, paper and cardboard, textiles, leather, wood, paints and articles made of plastic, and cooling lubricants. The shelf life of these preparations depends on their resistance to microbial spoilage. In addition, in many industrial applications, antimicrobial agents are useful in sealants, rope, paper pump, plastics, fuel, oil, and rubber and metal working fluids and as wood preservatives. The control of slime-producing bacteria and fungi in pump and paper mills and cooling towers is a matter of substantial commercial importance.

Examples of microorganisms which can effect contamination, degradation, or a change in the industrial environment and industrial and/or commercial materials are bacteria, fungi, yeasts, algae, and slime organisms. Microorganisms of the following genera are examples: *Alternaria*, such as *Alternaria tenuis*, *Aspergillus*, such as *Aspergillus niger*, *Chaetomium*, such as *Chaetomium globosum*, *Candida*, such as *Candida albicans*, *Lentinus*, such as *Lentinus tigrinus*, *Penicillium*, such as *Penicillium glaucum*, *Trichophyton*, such as *Trichophyton mentagrophytes*, *Aureobasidium*, such as *Aureobasidium pullulans*, *Enterobacter*, such as *Enterobacter gergoviae*, *Trichoderma*, such as *Trichoderma viride*, *Escherichia*, such as *Escherichia coli*, *Pseudomonas*, such as *Pseudomonas aeruginosa* and *Pseudomonas cepacia*, and *Staphylococcus*, such as *Staphylococcus aureus* and *Staphylococcus epidermidas*.

Copper (II) or cupric ethanolamine aqueous solutions have an important application in the preservation of wood, and in preventing insect and fungus attack. Formulations using this biocide formulation are used through the world. Among these commercial formulations are Copper Azole (Types A and B), Ammonical and/or Amine Copper Quat (Types B, C and D), and Copper HDO. Wood preservative formulations containing copper amine plus usually at least one additional co-biocide are intended to generate wood products, resistant to decay and insect attack, which are more environmentally friendly than the previously used preservative systems.

Copper ethanolamine solutions used in the wood preservation industry are made by dissolving either single components or mixtures of copper hydroxide, copper carbonate or basic copper carbonate. For example, U.S. Pat. Nos. 5,527,384 and 5,635,217 disclose dissolution of copper carbonates in aqueous ethanolamine solutions followed by addition of the co-biocides, tebuconazole or propiconazole. However, thermal drying of these solids frequently causes copper (II) or cupric oxide to form, which is insoluble in ethanolamine and undesirable in wood preservation formulations.

U.S. Pat. No. 6,489,037 describes a coating for inhibiting stain in floor coverings that includes a copper amine complex. Copper compounds as wood preservatives are described in U.S. Pat. No. 6,352,583. Timber preservatives including a copper compound and a polyamine are described in U.S. Pat. No. 6,110,263. Liquid wood preservatives comprising a complex of a copper cation and alkoxylated diamine are described in U.S. Pat. No. 5,426,121. Wood preservatives based on a copper compound an aliphatic acid and a polyamine are described in U.S. Pat. No. 4,857,322. Water soluble copper salts are described in U.S. Pat. No. 4,808,407.

A wood preservative comprising a chromated copper arsenate, ammoniacal copper arsenate or ammoniacal copper zinc arsenate in an oil emulsion is described in U.S. Pat. No. 4,950,329 to Hickson Corporation. A method for fixing chromated copper arsenate agents in wood is described in U.S. Pat. No. 4,942,064 to Hickson Corporation. U.S. Pat. No. 5,492,681 to Hickson Corporation describes a method for producing copper oxide using a copper bearing material and ammonia. U.S. Pat. Nos. 5,427,384 and 5,634,967 and Re. 36,798 to Hickson International Plc describe a wood preservative including a cuprammonium compound and tebucanozole.

The copper salts are made from a variety of copper sources. For example, commercial processes employ scrap copper metal, spent etching solutions from the microelectronics industries or other copper-rich solids or solutions. Copper metal can be dissolved in sulfuric acid followed by addition of sodium carbonate to generate the basic copper carbonate (BCC) (H. Remy, Treatise on Inorganic Chemistry, 1956, p 389). Similarly copper metal can be dissolved in ammonia/ammonium carbonate solutions followed by boiling off the ammonia to precipitate BCC. Copper hydroxide can be produced by the addition of sodium hydroxide to an aqueous solution of a copper salt, e.g., chloride, nitrate, etc.

Electrolytic methods have been described. For example J. Errera (Bull. Acad. Belg., (5), 1, 361, 1921) described the production of basic copper carbonate at the copper anodes having pasted a current through an aqueous solution of sodium bicarbonate.

PCT WO 01/51683 A1 discloses a galvanic method of accelerating copper dissolution in nitrogen compounds. This document discloses the use of a copper anode and a cathode of silver or similar material separated by a semi-permeable membrane, and an ethanolamine solution. Passing a galvanic current through the system resulted in copper dissolution into the aqueous ethanolamine solution. It is disclosed that a copper in ethanolamine solution was obtained, but took a very long time, e.g. 45 hours. This amount of time would be commercially undesirable and higher concentrations of copper would be commercially desired, than those taught.

Copper dissolution in amine solutions has been described. There has been considerable research published on the reaction kinetics of ammonia/ammonium salt aqueous solution with copper metal in the presence of oxygen to produce aqueous solution of the copper ammoniate salt. Kinetic studies were initiated by Yamasaki (E. Yamasaki, Sci. Rep. Tohoku Imp. Univ. Ser. I, 9, 169 (1920) and later by others (R. W. Lane and H. J. McDonald, JACS, 68, 1699 (1946); J. Halpern, J. Electrochem. Soc., 100, 421 (1953); J. I. Fisher and J. Halpern, J. Electrochem. Soc., 103, 282 (1956); B. C. Y. Lu and W. F. Gordon, JACS, 77, 6136 (1955); F. Habashi, Ber. Bunsengesellschaft physik. Chem., 67 (4), 402 (1963); Z. Zembura and A. Maraszewska, Roczniki Chem., 40, 1149 (1966). ibid, Polish J. of Chem., 59, 907 (1985); R. D. Williams and S. D. Light, American Inst. Chem. Eng., 21 (1978); Z. Zembura, A. Piotrowski, and Z. Kolenda, J. Applied Electrochem., 20, 365 (1990)).

Halpern (J. Electrochem. Soc., 100, 421 (1953)) reported a study of varying ammonia and ammonium salt concentrations, oxygen partial pressures, temperatures, stirring velocities and geometric surface areas of the metallic copper. Halpern stated that at low oxygen concentrations the rate of copper dissolution was determined by the transport of oxygen to the surface. At high oxygen concentrations the rate was determined by the chemical reaction at the copper surface.

U.S. Pat. No. 6,646,147 to Richardson discloses a process for producing a copper-containing aqueous monoethanolamine solution.

Present methods of producing copper ethanolamine solutions suffer from disadvantages including long reaction times and poor yield.

There is a need for useful and efficient methods for producing copper ethanolamine aqueous solutions.

SUMMARY OF THE INVENTION

Provided are processes, methods, and reactor systems for the production of copper ethanolamine aqueous solutions from metallic copper and ethanolamine. Also provided are preservation formulations or copper ethanolamine aqueous solutions that in one embodiment are used for the preservation of wood. As used herein, ethanolamine is used interchangeably with monoethanolamine.

It has been discovered that utilizing pure oxygen as an oxidant under pressurized conditions while optionally agitating the copper material produces significantly increased copper dissolution yields. While the applicants do not wish to be bound by any particular theory, it is thought that the pressurized reaction conditions, in combination with agitating the reactants, results in higher solubility concentrations of dissolved $O_2$ in solution, greatly enhancing the ability to dissolute copper on a commercial scale. High concentrations of the desired copper monoethanolamine can be obtained utilizing the disclosed processes, and these solutions can be optionally diluted to produce a variety of preservative formulations such as wood preservation formulations.

In one embodiment, a method of producing aqueous copper ethanolamine solutions is provided, the method comprising:
 reacting:
  i) copper metal;
  ii) oxygen;
  iii) an amine, such as an alkyl hydroxylamine, e.g., monoethanolamine; and
  iv) an acid or acid anhydride; to generate an amine salt, such as an ethanolamine salt.

In one embodiment, there is provided a method for the production of a copper ethanolamine solution in a vessel, comprising:
 a) providing in a vessel a mixture of:
  i) water;
  ii) an alkyl hydroxylamine, such as monoethanolamine;
  iii) an acid, acid anhydride or ethanolamine acid salt; and
  iv) a metallic copper bearing material;
 b) feeding oxygen, e.g., air or pure oxygen, into the mixture;
 c) maintaining the mixture at a temperature, e.g., of about 40-115° C., 40-100° C., 40-90° C., 40-80° C., 60-90° C., 70-90° C., 80-100° C. or 80-115° C., to dissolve the metallic copper; and
 d) optionally removing excess metallic copper or other extraneous solids from the dissolved copper alkyl hydroxylamine (such as monoethanolamine) solution, thereby to form the product.

The components of steps a) can be added in any order.

The reaction conditions, including pressure, temperature and reactant concentration, may be selected to promote rapid product formation. In one embodiment, air is used with a temperature of 40-90° C., 60-90° C. or 60-80° C. at atmospheric pressure or with higher applied pressure, such as 50 or 75 psig. In another embodiment, pure oxygen is used, with a temperature e.g. of 80-100° C., or 85-95° C. or 110° C. or 115° C. or higher, and the oxygen may be applied with a pressure, e.g., of 1, 5, 15, 20, 25, 35, 45, 50, 65, 75, 80, or 90 psig.

Also provided is a method for the production of an aqueous copper ethanolamine solution, comprising:
 a) providing in a vessel a mixture of:
  i) water;
  ii) monoethanolamine;
  iii) $CO_2$; and
  iv) a metallic copper bearing material;
 b) feeding oxygen into the mixture;
 c) maintaining the temperature of the mixture, e.g., at about 40-115° C., or, e.g., 60-90° C., to dissolve the metallic copper; and
 d) optionally removing excess metallic copper or other extraneous solids from the dissolved copper ethanolamine solution, thereby to form the copper ethanolamine solution product.

The carbon dioxide is present for example in an amount of about 5-30% by weight, or, for example about 8-12% by weight.

In an another aspect, a method of producing aqueous copper ethanolamine solutions is provided, the method comprising:
 reacting:
  i) copper metal;
  ii) an oxidant, such as air or pure oxygen;
  iii) an amine, such as an alkyl hydroxylamine, e.g., a monoethanolamine; and
  iv) an acid or acid anhydride;
wherein the oxidant is administered into the reaction under pressure to generate a copper amine salt, such as a copper ethanolamine salt. In one particular embodiment, pure oxygen is administered at a pressure of 1, 5, 20, 35, 50, 65, 75, 80, or 90 psig.

In still another aspect, a method of producing aqueous copper ethanolamine solutions is provided, the method comprising:

Reacting in an aqueous solution:
i) copper metal;
ii) an oxidant, such as air or oxygen;
iii) an amine; such as an alkyl hydroxylmine, e.g. monoethanolamine, such as monoethanolamine; and
iv) an acid or acid anhydride;

wherein the oxidant is administered into the reaction under pressurized conditions, and the copper metal is agitated in the solution. In one embodiment, the oxidant is pure oxygen administered to the reaction occurring in a reaction vessel at 1, 5, 20, 35, 50, 65, 75, 80, or 90 psig.

In one embodiment, there is provided a method for the production of a copper ethanolamine solution in a vessel, comprising:
a) providing in a vessel a mixture of:
i) water;
ii) an alkyl hydroxylamine, such as monoethanolamine;
iii) an acid, acid anhydride or ethanolamine acid salt; and
iv) a metallic copper bearing material;
b) feeding oxygen, e.g., air or pure oxygen, into the mixture under pressurized conditions such as 1, 5, 20, 35, 50, 65, 75, 80, or 90 psig.;
c) agitating the mixture;
d) maintaining the mixture at a temperature, e.g., of about 40-115° C., 40-100° C., 40-90° C., 40-80° C., 45-55° C., 60-90° C., 70-90° C., 80-100° C. or 80-115° C., to dissolve the metallic copper; and
e) optionally removing excess metallic copper or other extraneous solids from the dissolved copper alkyl hydroxylamine (such as monoethanolamine) solution, thereby to form the product.

The components of steps a) can be added in any order. The reaction conditions, including pressure, temperature and reactant concentration, may be selected to promote rapid product formation. Agitation levels can be adjusted so that the liquid-gas interface within the vessel is disturbed, preferably in such a way so that a portion of the liquid is dispersed through the gas head space of the vessel. In one embodiment, the liquid is dispersed through the gas head space via splashing induced by an agitator. Alternatively, the liquid can be dispersed through the gas head space by spraying the liquid through the headspace, or circulating the gas from the headspace into the liquid using a blower.

In one embodiment, diethanolamine or triethanolamine can be substituted for monoethanolamine.

Also provided is a method for the production of an aqueous copper ethanolamine solution, comprising:
a) providing in a vessel a mixture of:
i) water;
ii) monoethanolamine;
iii) $CO_2$; and
iv) a metallic copper bearing material;
b) feeding oxygen into the mixture under pressurized conditions such as 1, 5, 20, 35, 50, 65, 75, 80, or 90 psig.;
c) agitating the mixture;
d) maintaining the temperature of the mixture, e.g., at about 40-115° C., or, e.g., 60-90° C., to dissolve the metallic copper; and
e) optionally removing excess metallic copper or other extraneous solids from the dissolved copper ethanolamine solution,
thereby to form the copper ethanolamine solution product.

Advantageously, a desired concentration of dissolved copper can be obtained in the product, and the reaction conditions can be designed to shorten the reaction time required to produce a desired concentration. The dissolved copper concentration in the product is for example, 5 to 15 weight percent.

The mole ratio of carbon dioxide to copper is, e.g., in the range of 0.5 to 1.5 moles of carbon dioxide per mole of copper. One exemplary range is 0.7-0.8.

The mole ratio of alkyl hydroxylamine (such as monoethanolamine;) to dissolved copper in the product is, e.g., 2.0-5.0, 3.0 to 5.0, 3.0-4.0, or 3.5 to 4.0 moles of alkyl hydroxylamine per mole of copper.

The reaction may begin with an excess of copper metal, and a sufficient amount of copper metal can be used under the appropriate reaction conditions to obtain the desired ratio of dissolved copper to alkyl hydroxylamine in the product.

The reaction is conducted, e.g., at a temperature of about 40-115° C., or at 60-90° C. A temperature is selected to preferably obtain good reaction rates and preferably negligible to no by-product of oxidized ethanolamine. Optionally, the temperature is about 40-80° C., 40-60° C.; 50-60° C.; 60-80° C.; 65-80° C.; 70-80° C.; 70-90° C.; 80-100° C. or 90-110° C.

In particular, in one embodiment, the temperature is greater than 65° C.; greater than 70° C.; greater than 75° C.; greater than 80° C., or greater than 90° C. The selection of the appropriate temperature and other conditions as described herein permits the reaction times to be reduced and the concentration of dissolved copper in the product to be enhanced.

The anhydride used may be carbon dioxide. In addition to carbon dioxide, other acids or anhydrides can be used. Optionally, the acid, acid anhydride or ethanolamine acid salt is carbonic acid, carbon dioxide or a protonated ethanolamine carbonate.

In addition to air as the source of oxygen, pure oxygen can be used. Optionally the source of oxygen can be a pressurized source which bubbles the gas through the solution. In one embodiment, the oxygen is administered to the solution through a diffuser, such as a porous metal diffuser. The metallic copper bearing material is any copper bearing material including scrap or pure copper or, e.g., #1 or #2 scrap e.g., that is optionally bulk or chopped.

The reaction vessels used may be standard reactors, adapted with ports for the administration or removal of components including gases or liquids. Optionally the reaction is conducted in a reactor that is a stirred tank open to the atmosphere or under pressure. Preferably the reaction vessel is a tank capable of supporting agitation under pressure. The agitator can comprise any implement for stirring such as a mechanical agitator comprising a paddle or propeller, or any agitation device that provides sufficient agitation of a desired liquid or solid to be agitated. The reaction vessel may be a fixed bed, such as a column or tube, containing the metallic copper bearing material through which the heated solution reactants and air are passed. For example, the reaction vessel may be a column filled with the copper material through which a solution of the other reactants passes. The reaction vessel is optionally pressurized. The solution can be re-circulated, optionally at a constant rate, through the vessel.

The rate of formation of dissolved copper in the product can be enhanced by the methods disclosed herein. The dissolved copper concentration in the product is, e.g., optionally about 5-15, 8-12, or 9-10 weight percent copper. For certain applications, it is desirable to obtain a dissolved copper concentration of at least 8%, at least 9%, at least 10%, at least 11%, at least 12%, or, e.g., at least 15%, which is achieved by adjustment of the reaction conditions, including concentration of reactants, pressure and temperature. In one embodiment, a product with 10.2-10.3% copper is a target concentration with reduced reaction time. Often a concentrated solution is obtained which is diluted in the process of forming a desired formulation.

The appropriate conditions including temperature and pressure are selected to obtain the desired yield in the desired amount of time. In one embodiment, the method comprises combining water, monoethanolamine, $CO_2$, metallic copper, and oxygen at an appropriate temperature, pressure, and agitation level to obtain a copper ethanolamine aqueous solution with a concentration of at least 10-15% in less than about 12 hours, less than about 8 hours, less than about 7 hours, less than 5 hours, or, e.g., less than 3 hours. Alternatively, a copper dissolution rate of between 10-130 g/L-hr can be obtained, dependent on the temperature, pressure and agitation levels selected. Preferably, a copper dissolution rate of greater than 20 g/L-hr is obtained.

Other components can be added to the reaction mixture including amines such as polyamines, ammonia acids and nitrogen bases.

The reaction advantageously is conducted in the absence of the application of an electrical current or the use of a membrane.

An optimal pressure of oxygen in the reaction vessel may be selected. For example, the oxygen, in the form of air or pure oxygen, may be administered at a pressure of, e.g., 0, 1, 5, 20, 35, 50, 65, 75, 85, 90 psig or more.

In one embodiment, there is provided a reaction vessel comprising water, monoethanolamine, carbon dioxide, and a copper material, wherein the reaction vessel is pressurized, and wherein the reaction vessel further comprises an agitator. The agitator may be a mechanical agitator comprising one or more propellers for mixing copper in the reaction mixture, and/or for agitating the surface of the reaction mixture to disperse it into the gaseous phase comprising oxygen adjacent to the reaction mixture. The vessel also may further include a conduit, such as a tube, for delivering oxygen into the mixture. The conduit may include a diffuser through which the oxygen (including pure oxygen or air) is dispersed. Reactions as described herein may be conducted in the vessel.

DETAILED DESCRIPTION

Figure 1:
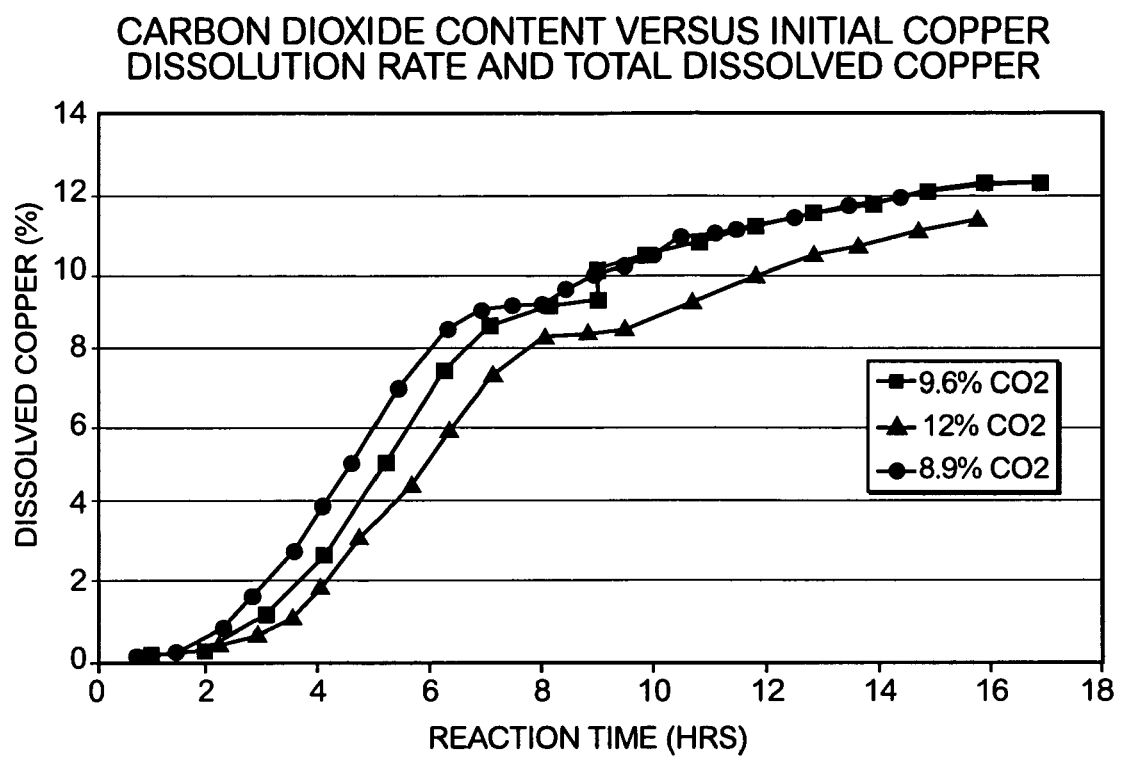
FIG. 1 is a graph of carbon dioxide content versus initial copper dissolution rate and total dissolved copper for a reaction of copper in an aqueous monoethanolamine solution.

Provided are processes and methods for the production of copper alkyl hydroxylamine aqueous solutions. Also provided are preservation formulations and methods that can be used in a wide range of applications. In one embodiment, the formulations are used for the preservation of wood. Copper alkyl hydroxylamine aqueous solutions are provided that can be formed from metallic copper and ethanolamine. In particular, methods are provided for the production of copper monoethanolamine aqueous solutions from metallic copper and monoethanolamine.

In a first embodiment, there is provided a method for production of copper ethanolamine solution in a vessel by combining in the vessel:
  i) water;
  ii) an alkyl hydroxylamine, such as ethanolamine;
  iii) an acid or acid anhydride, to generate an acid salt of the alkyl hydroxylamine; or an acid salt of the alkyl hydroxylamine, such as ethanolamine; and
  iv) a metallic copper bearing material.

As used herein, the alkyl hydroxylamine is, for example monoethanolamine, diethanolamine, or triethanolamine.

A source of oxygen, such as air or pure oxygen, is fed into the mixture. The oxygen can be fed into the mixture at a pressure for example, of 1, 5, 10, 15, 20, 25, 35, 45, 50, 65, 75, 85, or 90 psig. The temperature of the mixture is controlled to a suitable temperature, e.g., about 40° C.-115° C., or 40° C. to 90° C. to dissolve the metallic copper, thus forming an aqueous copper monoethanolamine solution. Excess metallic copper or other solids can be removed, e.g, by filtration. Additionally, the mixture can be agitated to, for example, stir copper metal in the solution. In embodiments where the reaction occurs in a pressurized reactor with pure oxygen applied under pressure, then it is advantageous to use an agitator to stir the solution to cause dispersal of the solution into the gaseous phase above the solution to absorb more of the reactive oxygen into the solution.

In a second embodiment, the method of producing a copper ethanolamine solution comprises combining:
  i) water;
  ii) ethanolamine;
  iii) an acid or acid anhydride, such as $CO_2$, which can react with a portion of the ethanolamine to generate the ethanol ammonium carbonate salt; and
  iv) a metallic copper bearing material.

A source of oxygen, such as air, is fed into the mixture. The oxygen can be applied to the reaction solution in a reaction vessel at a pressure for example, of 1, 5, 10, 15, 20, 25, 35, 45, 50, 65, 75, 85, or 90 psig. The temperature of the mixture is controlled at a suitable temperature, e.g., about 40-115° C., or 60-100° C. or 90° C.-110° C. to d the metallic copper, thus forming the aqueous copper ethanolamine solution. Excess metallic copper or other solids can be removed, e.g, by filtration. An agitator can be used to agitate the copper metal, and/or the solution.

As noted above, the reaction components include the alkyl hydroxylamine and water. The reaction mixture further includes an acid salt of the alkyl hydroxylamine, which is optionally generated in situ. The acid salt can be generated by reaction of a portion of the alkyl hydroxylamine with an acid or acid anhydride, to form the salt thereof.

For example, the reaction components may include ethanolamine and the anhydride, $CO_2$, which react to form the ethanolammonium carbonate salt while still leaving a portion of the ethanolamine available for reaction with the copper.

The acid that reacts with the alkyl hydroxylamine to form the acid salt of alkyl hydroxylamine is, e.g., an inorganic acid, such as sulfuric acid, nitric acid or hydrochloric acid, or organic carboxylic acids, such as acetic, glycolic, tartaric, fumaric and maleic acid. For example, the acid salt of ethanolamine is optionally generated by reacting ethanolamine with, e.g., sulfuric acid, glycolic acid, nitric acid or hydrochloric acid. In one preferred embodiment, the acid salt of ethanolamine is generated by combining ethanolamine with $CO_2$.

Other acids that can be used include polyphosphoric acids, such as tripolyphosphoric acid, aminocarboxylic acids such as glycine, glutamic acid, ethylenediaminetetra-acetic acid, hydroxyethyldiamine triacetic acid, nitrilotriacetic acid and N-dihydroxy ethylglycine; hydroxycarboxylic acids such as tartaric acid, citric acid, malic acid, lactic acid, hydroxybutyric acid, glycolic acid, gluconic acid and glucoheptonic acid; and phosphonic acids such as nitrilotrimethylene phosphonic acid, ethylenediaminetetra (methylene phosphonic acid), and hydroxyethylidene diphosphonic acid.

In one embodiment, the molar ratio of carbon dioxide to copper is about 0.5 to 1.5, or about 1.0 to 1.3, or about 0.7-0.8 moles of carbon dioxide per mole of copper.

The molar ratio of ethanolamine to dissolved copper in the product is, e.g., about 2-5, 3 to 5, 3.5-4.0, or about 3-4, or e.g. about 3 to 3.8 moles of ethanolamine per mole of copper.

The concentration of dissolved copper in the product will depend on reaction conditions. A dissolved copper concentration in the product can be obtained, which is, e.g., 5-15%, 7-15%, 9.0-12%, 9.0-15%, 12-13%, or 12-15% by weight. A di copper concentration of at least 8%, at least 9%, at least 10%, at least 11%, at least 12%, at least 13% or, e.g., at least 15% can be obtained by adjustment of the reaction conditions, including concentration of reactants, pressure and temperature, as described herein. In one embodiment, the dissolved copper concentration is at least about 12-13% or 12-15% for use in diluting to form commercial formulations with further components.

These solutions in one embodiment are void of solids and optionally contain no to only negligible amounts of copper (I) or cuprous ion, for example less than one percent of the total copper percentage. These solutions preferably are stable at ambient temperatures for extended periods of time, such that preservative formulations comprising the solutions plus additional co-biocide(s) are sufficiently stable from commercial use.

The reaction is conducted, e.g., at a temperature of about 40-110° C., 60-100° C., 40-90° C., or, e.g., 60-70° C. A temperature is selected to preferably obtain good reaction rates and negligible to no by-product oxidized ethanolamine. Optionally, the temperature is about 40-60° C.; 50-60° C.; 60-80° C.; 65-80° C.; 70-80° C. or 70-90° C. In particular, in one embodiment, the temperature is at least 60° C.; at least 80° C., or at least 90° C., to enhance the speed of the reaction and the yield of dissolved copper.

The selection of temperature will be based on the other reaction conditions and the desired concentration of dissolved copper in the product. When using lower purity oxygen, e.g., air, the reaction time may be longer, and therefore a lower temperature, such as 40-80° C. may be used, to avoid oxidation. However higher temperatures may also be used for example with shorter reaction times. When higher purity oxygen gas is used, the reaction time is reduced, and higher temperatures can be used, for example 70-110° C. Moreover, as the pressure of oxygen in the reaction is increased, the reaction times are reduced, and higher temperatures can be used.

In the reaction, the oxygen, e.g. in the form of air or pure oxygen, can be applied under pressure, e.g. 0, 1, 5, 10, 15, 20, 25, 30, 35, 40, 45, 50, 60, 65, 70, 75, 80, 85, or 90 psig to enhance the yield and/or reduce reaction time. In one embodiment, the oxygen is applied to the mixture under pressure through a diffuser, such as a porous metal diffuser.

An optional temperature when applying air at 50 psi is about 60-85° C. Using air, an optional temperature at 75 psi is about 60-70° C., or 60-85° C., or 85-90° C. Using pure oxygen, an optional temperature when applying pure oxygen at 50 psi or 75 psi is about 80-110° C.

The aqueous copper ethanolamine solutions are useful for wood preservation in a variety of applications. Copper, in the form of a water-insoluble compound (e.g. copper carbonate, BCC, copper hydroxide, etc.), can act as the biocide, while ethanolamine can act as the solubilizing agent in the copper compound. Thus, a reduction in the solubilizing agent reduces the overall cost of the copper biocide.

Optimized Reaction Conditions

The reaction conditions can be optimized to enhance the yield of copper monoethanolamine aqueous solutions, by modifying, e.g., concentration, temperature, and pressure.

For example, the reaction can be conducted at a temperature of at least 65° C. to produce a solution with a dissolved copper concentration of at least 11%, 12% or at least 15% in less than 12 hours, 6 hours, 4 hours or 3 hours.

The reaction can be conducted at atmospheric pressure in a reactor using air as the source of oxygen. In this embodiment, the reaction of copper, ethanolamine, acid or anhydride, such as $CO_2$ and air is conducted at a temperature, for example, of about 60-80° C. for about 6-8 hours to produce at least 8% or 9% percent dissolved copper by weight, or e.g. at least 10, 11, 12, 13, 14, or 15%. In certain embodiments, it is preferred to produce a concentration greater than 10% so that the solution can be diluted to form a diluted secondary product solution with e.g., a concentration of 9.0-10%.

In one embodiment, copper dissolution rates are between 10-130 g/L-hr, or greater than 20 g/L-hr.

In another embodiment, formation of the desired concentration of dissolved copper in the product is accelerated by conducting the reaction under pressure, and/or increasing the concentration of oxygen (e.g. by using pure oxygen). By increasing the temperature (to e.g., at least 70° C., 80° C., at least 90° C. or at least 100° C.), the reaction time can be reduced to, e.g., less than 8 hours, less than 6 hours, less than 4 hours or less than 3 hours, and the dissolved copper in the product can be any desired amount e.g., at least 10, 11, 12, 13, 14 or 15% by weight. The reaction is conducted for a sufficient amount of time to provide the desired concentration of dissolved copper in the product.

Additionally, the mixture can be agitated to disperse solid copper material through the mixture. Agitation also can be used to increase the concentration of dissolved oxygen in the mixture, further reducing reaction time and increasing copper dissolution. For example, the mixture is agitated so that the liquid-gas interface of the vessel is disturbed, so that the liquid is sprayed or diffused into the air or oxygen over the mixture to allow the mixture to absorb more oxygen. While the applicants do not wish to be bound to any one theory, it is thought that disruption of the liquid-gas interface in the vessel head space increases exposure of the liquid to oxygen, further improving absorption of oxygen into the liquid.

The concentration of ethanolamine can have an impact on the reaction. Exemplary useful concentrations of ethanolamine in water are about 10-60, 25-50 or 30-45 percent by weight.

The concentration of carbon dioxide can impact the reaction. In one embodiment, the reaction of copper, ethanolamine, $CO_2$ and oxygen is conducted. The mole ratio of carbon dioxide to copper is, e.g., in the range of 0.5 to 1.5. An exemplary range is 0.7-0.8. Alternatively, a stoichiometric amount of $CO_2$ can be used. Alternatively, the mole ratio of carbon dioxide to copper is about 0.7-0.8. The reaction, for example, can take about 6-8 hours to produce at least 8, 9, 10 or 11 percent dissolved copper under these conditions with air at atmospheric conditions.

The pressure of the oxygen (e.g. air or pure oxygen) can be adjusted to optimize the reaction. In one embodiment, the reaction of copper, monoethanolamine, $CO_2$ and oxygen is conducted wherein the oxygen, e.g. in the form of air, is applied under pressure, e.g. 20, 50, 75 or 90 psig to enhance the yield or reduce reaction time. The reaction can occur in a reactor with a flow through system to maintain the pressure. The reaction, for example, can take about 5-8 hours, 8-10 hours or 8-12 hours to produce at least 8, 9, 10, 12 or 15 percent dissolved copper by weight under these conditions.

By using air under pressure, the reaction time is reduced, e.g. by 30%. The use of pure oxygen, increased pressure, and agitation can further reduce reaction time. In one embodiment, the reaction conditions, such as temperature and/or pressure and/or the use of pure oxygen and/or agitation, are selected to reduce the reaction time to, e.g., less than 2, 3, 4 or 5 hours.

Examples of particular embodiments include conducting the reaction at 75 psig using air at 60° C. -90° C. to obtain a product with at least 10% dissolved copper in less than about 5 hours.

In another embodiment, the reaction is conducted using 25-75 psig pure oxygen in a pressurized reaction vessel at 70-90° C., or 90-110° C. to obtain a product with at least 10% dissolved copper in at least 2.5-3.0 hours.

For example, the pressure of oxygen is at least 5, 10, 20, 25 psig, 30 psig, 40 psig, 50 psig, 60 psig, 70 psig, 80 psig, or 90 psig, to produce a copper ethanolamine aqueous solution with a dissolved copper concentration of at least 9, 10, 11, 12, 13, 14 or 15 percent by weight with a reaction time less than 2, 3, 4, 5, 6, 7, 8, 9, 10 or 12 hours.

In one embodiment, the reaction is conducted with a "heel" of 1-2% of dissolved copper product, for example, from a previous run in a reactor. This advantageously can reduce the reaction time. For example, using a 1-2% heel, with a reaction temperature between about 65° C. to 85° C. or at least 90, 100 or 110 ° C., in about 4-4.5 hours, a product can be obtained with a dissolved copper concentration of at least about 10% at 75 psig, or 4-6 hours at 50 psig. The presence of a heel of a small amount of residual product copper in the reaction vessel, at a concentration e.g. of 1-2%, can reduce the reaction time to, e.g., 6 hours or less. With the heel, for example, at 85° C., 90° C., 100° C. or 110° C., at 75 psig the reaction time can be reduced to 4 hours, or 5 hours at 50 psig, to produce concentrations of dissolved copper in the product of greater than 8%. This is advantageous because the reaction time is reduced. Air or pure oxygen can be used, and the reaction will proceed more quickly with the use of pure oxygen.

In one embodiment, the reaction includes a 1% Cu heel at 85° C. at 75 psig, using air as the source of oxygen, to produce a 10.5% copper solution in 5 hours. Contrastingly, at atmospheric pressure, the reaction may take 8, 10 or 11 hours. Thus, the use of higher pressure is advantageous.

In a particular embodiment, the process can be initiated by adding the desired amount of ethanolamine to water in a stirred reaction vessel, with port(s) open to the atmosphere. The ethanolamine concentration can vary, e.g., between 30 and 60 weight percent, or between 40 and 55 weight percent. The carbon dioxide can be added to the aqueous ethanolamine solution such that the resulting concentration will range between 5 to 15 weight percent, or, e.g., between 6 to 10 weight percent. Copper metal is charged to mix, and the mixture maintained at a temperature of about 40 to 110° C., e.g. 60-70° C. or 80-100° C., with air sparge at a rate sufficient to pass all the chemically required oxygen to the unit in 6 to 24 hours, e.g. 10 to 12 hours or less.

The reaction is optionally conducted by passing a solution of reactants through a flow through vessel which may be a tube or column containing the copper metal, optionally supported on a screen. This method advantageously overcomes the problem that occurs with trying to stir large amounts of copper metal in large reactors, where the contact of the solution with the surface copper metal may be diminished. Pressure and temperature control elements can be applied to the vessel to control the temperature of the solution. For example, a heated jacket or a cooling element may be applied to the vessel, allowing the solution passing through the vessel to be maintained at a desired temperature. The reaction mixture can be recycled or re-circulated through the vessel, optionally at a constant rate, to enhance the yield and more efficiently expose the solution to the copper metal.

In contrast, if the reaction is done in a reactor with agitation, then the agitator can be used to disperse the copper metal. This may be difficult if there is a large amount of copper metal to be agitated, however selection of the appropriate agitator and amount of copper can allow for successful agitation.

The time necessary for completion of reaction will vary depending on conditions including the oxygen pressure, size of copper particles used, temperature of reaction, stir rate or flow, agitation level, purity of starting materials, and ethanolamine concentration as well as carbon dioxide concentration. Under selected conditions, the reaction is completed in e.g. less than 2 hours, less than 3 hours, less than 4 hours, less than 6 hours, less than 8 hours, less than 12 hours, less than 14 hours, less than 16 hours, less than 24 hours, or less than 2 days. The optimal stir rate or flow rate can be determined for a process design.

The results described herein are surprising since it might be anticipated that the rate of copper dissolution into an ethanolamine solution would be slower than in the ammonia solutions due to steric hindrance caused by the 2-hydroxyethyl group of the ethanolamine, and because ethanolamine is readily oxidized by copper (II) or cupric moieties, because the hydroxide of the ethanolamine is susceptible to oxidation, and increasing the temperature to enhance the rate of copper dissolution in ethanolamine solutions could result in ethanolamine oxidation.

An unexpected mole ratio of copper to ethanolamine was found to be useful. Copper bonds to four nitrogen atoms when bonding with ammonia. It might be expected that this would be the mole ratio of copper to ethanolamine; however, mole ratios of e.g., 2 or 3.0, or e.g., 3.5 copper to ethanolamine are also suitable. This is useful since it can reduce the cost of the copper ethanolamine formulation such as a biocide formulation.

The pH of the reaction is for example, 8-11.5, or 8-11.3, or 8-11, or 9-11, or 9-10 The concentration of $CO_2$ is, e.g., 5-30% by weight. The concentration of monoethanolamine is, e.g., 30-40% by weight. An excess of copper material can be present. The oxidant can be present in a suitable amount for the reaction conditions.

Copper Source

Any copper bearing material can be used in this process. In one embodiment, pure metallic copper is used. Impure forms of copper, such as #1 and #2 scrap copper metal, can also be used. Ultra high purity cathode grade chopped copper, and other highly pure forms can be used. #1 Scrap copper metal typically contains approximately 99% copper, and #2 scrap metal typically contains approximately 97% copper, but this can vary somewhat among suppliers. #2 Scrap metal is often recycled copper wire that has been stripped of its insulation, and chopped into particles.

High purity starting materials, including high purity copper, can be used, or lower grade copper, which is less expensive than metallic copper, can be used if a certain amount of impurity can be tolerated in the final product.

The form of copper metal used can have a large geometric surface area, such as is found in commercial "fine" and "heavy" copper materials. These copper materials are predominantly chopped copper material including chopped copper wire and miscellaneous milled or sized copper scrap. The purity of the copper can vary from commercial #1 (high purity, 99+%) to #2 (typically >95% copper) or lower grades containing less than 95 percent copper.

In one embodiment, high surface area copper is used, such as finely divided copper metal with increased surface area. Chopped copper wire can be used in one embodiment.

Oxygen

Any source of oxygen, including air, can be used in the process. In one embodiment when using a closed vessel, pure oxygen is used. In an open vessel, lower concentrations of oxygen can be used.

Oxygen (any source thereof) can be introduced into the reaction mixture in any appropriate manner, e.g., under the surface of the reaction mixture. The gas should be introduced at a positive pressure with respect to the internal pressure of the vessel to prevent back-up of the mixture into the gas pipe. The upper bound on the gas pressure is limited only by the ability of the vessel to withstand the pressure and the flammability of the gas mixture produced. In one embodiment, the oxygen is introduced into the vessel at a pressure of about 5 and 100 psig, or about 20-40 psig, 30-50 psig, 50-60 psig, 60-70 psig, 70-80 psig, or 80-90 psig. The oxygen (e.g. in the form of air) pressure will affect the rate of reaction. For example, the pressure may be 0 psig, 20 psig, 50 psig, 75 psig or 90 psig.

In one embodiment, the stoichiometric amount of oxygen needed for reaction is calculated based on the weight and purity of the copper charged to the vessel, and the specified amount of oxygen, or a calculated excess, introduced into the vessel. In an alternative embodiment, oxygen is introduced until it is determined that the reaction mixture has stopped absorbing the gas. The amount of oxygen that has reacted with copper ion can be determined by weighing the reaction mixture before and after oxygen introduction.

The oxygen can be introduced into the reaction mixture in any way known in the art. Any device capable of sparging, bubbling, or diffusing the oxygen through the liquid interface can be utilized, such as a single element or multiple element side mounted diffusers, single element dip legged diffusers, single element flanged side mounted diffusers, manifold dip leg mounted diffusers, cross tank flanged side mounted diffusers, side streamed spargers, intrusive tangential spargers, pipe mounted intrusive spargers, dynamic pipeline spargers, porous metal diffuser, a coarse bubble, high volume horizontal format diffuser, Plenum chamber diffuser, membrane check valve diffuser, ceramic diffuser, or any other type of diffuser known in the art. Optionally, the device is a diffusing device that generates fine bubbles, such as a porous metal diffuser, or other appropriate diffusing device. Advantageously, the oxygen can be in one embodiment diffused into the solution, for example, below the copper.

Temperature and Time of Reaction

The reaction components are maintained at a sufficient temperature to form the dissolved copper product, e.g., 40-115° C., or 60-90° C. A temperature is selected to preferably obtain good reaction rates and negligible to no by-product oxidized ethanolamine. Optionally, the temperature is about 40-60° C.; 50-60° C.; 60-80° C.; 70-90° C.; or 80-110° C. In particular, in one embodiment, the temperature is at least 65° C.; at least 70° C.; at least 75° C.; or at least 80° C., to promote formation of dissolved copper. As noted herein, the temperature will also depend on the choice of other reaction conditions, such as pressure and source of oxygen. During the reaction, the reaction vessel can be heated or cooled by any appropriate means to maintain the temperature in this range, for example, a water jacket.

Reactor Design

A variety of reactor designs can be used. The reactor systems for producing copper ethanolamine aqueous solutions can include, e.g., reaction vessels, stirrers, agitators, gas sources, inlet and outlet valves, pressurized systems, inlet and outlet lines, thermocouples, heaters, agitators, gas diffusers, tanks, pumps, cooling jackets, scrubbers, steam sources, etc. The reactor systems described herein can be used in any of the reactions described herein, and the discussion of systems for the production of copper ethanolamine aqueous solutions is provided by way of example. Particular embodiments are described in Example 8 and shown in FIGS. 6, 7 and 12.

Any size reactor may be used with agitation or flow through. For example, the reactor may be 1000 gallon, 5000 gallon, 10,000 gallon, 15,000 gallon or higher.

For example, the reactor system can allow the reaction to undergo at atmospheric pressure in a large scale reactor. During operation, reactants are delivered to a 30 gallon reactor and the weight can be measured using a scale. The large scale reactor may be provided with the water and monoethanolamine, as well as the metallic copper bearing material, such as chopped copper metal, and then $CO_2$ and oxygen, e.g. in the form of air or pure oxygen, can be diffused through the solution, for example by a porous metal diffuser. The temperature of the reactor solution is controlled with the necessary components including heaters and coolers to the desired temperature, e.g., about 60-115° C., or 70° C.-90° C., to dissolve the metallic copper and to form the copper monoethanolamine solution, which is optionally filtered.

In another embodiment, heated components of the reaction solution are passed through a flow through vessel that can be a column or tube containing the copper metal. The reactor system can include a reactor vessel, a gas sparger tube or diffuser, an agitator for stirring, heater and cooling elements, pumps, air sources, inlets and outlets, and the tube or column containing chopped copper metal. This system permits copper metal to be provided in a flow through vessel, with e.g. a metal filter mesh supporting the copper in the tube, to enhance the contact of the solution with the metal without the requirement of agitation.

To conduct the reaction, in one embodiment, the water and monoethanolamine is provided in the reactor vessel, and the air and $CO_2$ are delivered to the solution, e.g., using a diffuser, and the mixture is optionally mixed with an agitator. The solution may be heated with the heater and passed via the pump upward through the copper filled column to react with the copper. This is an efficient method and can improve the yield and reaction time. For example, the reaction time may be less than 5, 6, 7, 8 or 9 hours. The liquid can be re-circulated through the column, optionally at a constant rate. Liquid rising through the column can pass through an overflow back into the reactor and optionally recycled through the column.

In another embodiment, the reaction is conducted in a pressurized reactor. Increasing the pressure of the system can improve the yield and reduce the reaction time. For example, the pressure of the oxygen is introduced into the vessel is, e.g., 5-100 psig, 20-40 psig, 30-50 psig, 50-60 psig, 60-70 psig, 70-80 psig, or 80-90 psig. The oxygen (e.g. in the form of air) pressure will affect the rate of reaction. For example, the pressure may be 0 psig, 20 psig, 50 psig, or 90 psig, to reduce the reaction time to, e.g., less than 5 hours, or less than 6, 7, 8, 9, 10 or 12 hours.

In one embodiment, water, $CO_2$ and monoethanolamine are charged to a reactor tank which contains copper metal. Pressurized air is pumped through the copper metal/solvent blend and the copper dissolves. When the reaction is completed, the solution is pumped to a second vessel where the balance of the $CO_2$ and water is added. The system may further include coolers and heaters to maintain a preferred temperature of the solution as described herein. Another embodiment is a premix reactor containing the MEA (monoethanolamine), $CO_2$ and water that is pumped, under pressure, through copper metal that is contained in a second reactor that may not be agitated.

In one embodiment, there is provided a reaction vessel comprising water, monoethanolamine, carbon dioxide, and a copper material, wherein the reaction vessel is pressurized, and wherein the reaction vessel further comprises an agitator. The agitator may be a mechanical agitator comprising one or more propellers for mixing copper metal in the reaction mixture, and/or for agitating the surface of the reaction mixture to disperse it into the gaseous phase comprising oxygen adjacent to the reaction mixture. The vessel also may further include a conduit, such as a tube, for delivering oxygen into the mixture. The conduit may include a diffuser through which the oxygen (including pure oxygen or air) is dispersed. Reactions as described herein may be conducted in the vessel.

Agitation

A variety of agitation levels and agitators can be used in the present invention. Agitators can be used to disperse copper metal through the reaction mixture. In one embodiment, the agitation level creates a disruption sufficient to cause a continuous splashing of the liquid at the liquid-gas interface, or a continuous or intermittent spraying of the liquid into the gas phase in the vessel head space.

Any agitator sufficient to induce liquid-gas interface interaction can be used in the present invention. The agitator can be or can comprise, for example, a mechanical agitator comprising a stirrer with one or more bars, a paddle or multiple paddle, a fin or multiple fin, a propeller or multiple propellers, an impeller or multiple impellers, a vertical mixer, a bottom entry mixer, or a side entry mixer. Useful agitators can comprise, for example, a turbine agitator, a multiple turbine agitator, a double contrary motion agitator, a single contrary motion agitator, a circulator dispenser, a fixed mount agitator, a portable agitator, a horizontal agitator, a ribbon agitator, or any other type of agitator known in the art. Other devices known in the art to create agitation of a mixture may also be sufficient.

Chemistry of Reaction

The chemistry for the reaction of copper in aqueous ethanolamine solutions containing dissolved carbon dioxide with oxygen can be broken down into the following equations, where EA is ethanolamine.

Overall Reaction $Cu + \frac{1}{2}O_2 + CO_2 + 3.5\text{-}4\ EA \rightarrow Cu(EA)_{3.5\text{-}4}CO_3$ (I)

Oxidation/Reduction Reaction Steps $Cu + 3.5\text{-}4\ EA \rightarrow Cu(EA)_{3.5\text{-}4}^{2+} + 2\ e^-$ (IIa)

$\frac{1}{2}O_2 + H_2O + 2\ e^- \rightarrow 2\ OH^-$ (IIb)

Neutralization/Anion Formation $CO_2 + H_2O \rightarrow H_2CO_3$ (IIIa)

$H_2CO_3 + 2\ OH^- \rightarrow CO_3^{2-} + 2\ H_2O$ (IIIb)

The hydroxide ion must be neutralized in this reaction, since it has been found to impede the overall rate of the reaction (Schweizer, J. Prakt. Chem., 76, 344 (1859)).

Formulations

A variety of formulations of aqueous copper ethanolamine solutions are provided. The formulations can be prepared as described herein and using methods available in the art. For example, the formulations may be in a form suitable for use as wood preservative formulations.

In the formulation, the dissolved copper can be, for example: 5-15%; 7-15%; or e.g. 9-12% by weight. The dissolved copper concentration can be, e.g., at least 7%, 8%, at least 9%, at least 10%, at least 11%, or, e.g., at least 12% by weight.

The formulations may further include one or more additives including co-biocide(s). The solutions can be formulated to be sufficiently stable for commercial use. Exemplary additives include propiconazole, didecyldimethyl ammonium chloride or carbonate (DDAC), benzalkonium chloride (BAC) and tebuconazole.

These solutions preferably are stable at ambient temperatures for extended periods of time, such that wood preservative formulations comprising the solutions plus additional co-biocide(s) are sufficiently stable for commercial use.

Applications for Preservation of Materials

The copper ethanolamine solutions and formulations thereof can be used as preservatives in a wide range of applications and for a wide range of materials. They can be used for the preservation of cosmetics, personal care products, household products, and industrial materials such as adhesives, sizes, paper and cardboard, textiles, leather, wood, paints and articles made of plastic, and cooling lubricants and other materials which can be attacked or decomposed by microbes and/or fungi. Components of production plants, for example, cooling water, which can be impaired by multiplication of microbes and/or fungi, may also be treated. Also, the integrity of other water-containing systems, such as swimming pools and spas, can be maintained by use of the preservatives. In addition, they can be used to control and eliminate microbes and/or fungi by disinfection and sanitization of surfaces, such as found in homes, institutions, and hospitals.

In one embodiment, a preservative composition is used in personal care products such as shampoos, conditioners, hair care products, creams, lotions, cosmetics, soap, skin care products; or household products such as laundry detergents, hard surface cleaners, and fabric softeners. In an alternative embodiment, the preservative composition is used in industrial products and materials, such as adhesives, sizes, paper and cardboard, textiles, leather, wood, paints and articles made of plastic, cooling lubricants. In addition, in many industrial applications, the preservative composition can be used in sealants, rope, paper pump, plastics, fuel, oil, and rubber and metal working fluids and as wood preservatives. Therefore, in one embodiment, the preservative composition can be used for the treatment of materials, including cellulosic materials. In one embodiment, preservative compositions are provided having the property of providing stain resistance to wood. The preservative composition also can be used in controlling the slime-producing bacteria and fungi in pump and paper mills and cooling towers.

Preservative compositions may have a wide range of utility for protecting against or controlling microorganisms from a wide variety of classes including fungi, bacteria, algae, viruses and yeasts. Some of the utilities of the compositions are to protect wood, paint, adhesive, glue, paper, textile, leather, plastics, cardboard, lubricants, including metal working fluids cosmetics, caulking, and industrial cooling water from microorganisms. The compositions can be suitable for use as plant protection agents, such as fungicides. Fungicidal agents in plant protection can be employed for combating Plasmodiophoromycetes, Oomycetes, Chytridiomycetes, Zygomycetes, Ascomycetes, Basidiomycetes and Deuteromycetes.

In the embodiment where wood is treated, the compositions and methods can provide enhanced sapstain resistance while also providing effective resistance to mold, mildew, soft rot, brown rot and white rot, and insect attack, including termites. The preservative compositions may be applied to any wood substrate, such as any hardwood or softwood.

For example, for preventing or controlling sapstain and mold, the wood preservative composition is applied to green wood. The term "green" as used herein is defined as freshly cut, unseasoned, or the like. Examples of suitable wood substrates include, but are not limited to, maple, oak, birch, cherry, fir, and the like. The wood preservative compositions may be applied to any wood substrate that is for example to be pressure treated. The wood substrate may be a soft wood, such as a pine, fir, or hemlock. Suitable pine wood substrates include, but are not limited to, southern yellow pine and ponderosa pine.

The compositions may be used in connection with a wide variety of hardwoods, softwoods and wood products. It is particularly advantageous for products which will be employed in potentially adverse conditions such as outdoors. Examples of specific end uses for products to be treated by the invention are utility poles, railroad ties, and building products used for decks, fences, foundations, roofs, boat docks, piers, walls and boardwalks.

The solutions may be employed advantageously with woods such as southern yellow pine, Douglas-fir, hem/fir, Jack pine, western pine, oak, hickory, maple, pacific fir, red pine, hemlock and spruce-pine fir. The compositions may be employed on raw material or finished wood products.

Wood or other material may be treated with the disclosed compositions. Further materials that can be treated include cellulosic materials such as cotton, as well as leather, textile materials, synthetic fibres, Hessian, rope, and cordage.

The compositions may also be applied as an additive to paints and similar materials that are susceptible to fungal degrade. Other materials include metal working fluids where stability of active ingredients can be a problem resulting in fungal infestation.

Another embodiment is a method of controlling microorganisms, such as fungi and sapstain organisms, on and/or in a wood substrate comprising applying a biocidally effective amount of the wood preservative composition to the wood substrate. The term "controlling" as used herein includes, but is not limited to, inhibiting the growth of microorganisms, such as fungi and sapstain organisms. Non-limiting examples of fungi are *Trametes versicolor* (*T. versicolor*), *Gloeophyllum trabeum* (*G. trabeum*), *Poria placenta* (*P. placenta*), *Lentinus lepideus* (*L. lepideus*), *Coniophora puteana* (*C. puteana*), and *Chaetomium globsum* (*C. globsum*).

Another Embodiment

One group has described the process of the invention as a process for producing a copper-containing aqueous solution, comprising dissolving a copper mass in the presence of an oxidant in an aqueous leach liquor containing monoethanolamine and $(HMEA)_2CO_3$, wherein the leach liquor is produced by partially carbonating the monoethanolamine, wherein the oxidant is air or oxygen. The amount of carbon dioxide introduced during the process can be controlled such that partial carbonation occurs to form $(HMEA)_2CO_3$. The process is optionally carried out at a temperature of 40-80° C. or 45-55° C. Optionally, the leach solution is re-circulated at a constant rate, or at a constant rate of about one tenth of the leach solution volume per minute.

The leach liquor is produced by partially carbonating the monoethanolamine, and may be generated externally of the dissolver or in situ in a chamber through the addition of carbon dioxide to the monoethanolamine/water solution by sparging or bubbling into the chamber.

In one embodiment, the carbon dioxide is present in an amount of about 5-30% by weight, for example about 8-12% by weight. In one embodiment, the monoethanolamine is present in an amount of about 30-40 weight %, or 35-38 wt. %. In one embodiment, the aqueous leach solution comprises about 36 wt. % MEA and about 10% by weight carbon dioxide. The oxidant, typically air or oxygen, can be introduced in the range of 2-20 standard cubic feet per hour (SCFH) for a 1 liter chamber. The process may be carried out at atmospheric pressure and at a temperature of 25-100° C., for example 45-65° C., and typically 45-55° C. The pH is for example maintained in the basic region, i.e. greater than 7, and is usually from about 8.0-11.3, more usually 9-10. The pH is usually maintained by addition of carbon dioxide as acid, or MEA as base.

The monoethanolamine complex of copper carbonate solutions can be prepared by dissolving the copper mass in a monoethanolamine/$CO_2$/$H_2O$ solution. The dissolution may be carried out in a batch dissolver, or may be performed as a continuous process in towers packed with copper. The copper and MEA/$CO_2$/$H_2O$ solution can be charged into the dissolver, and the circulation pump, air-flow and temperature controller can be actuated. The leach solution can be re-circulated in the reactor. The re-circulation can be carried out at a constant rate, and may be, for example, a constant rate of about one-tenth of the leach solution volume per minute.

One group describes the equation that represents the overall reaction as follows:

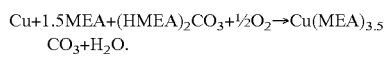

One group describes the equation that represents the in situ or external partial carbonation of the monoethanolamine as follows:

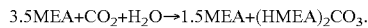

The carbon dioxide is optionally present in an amount of about 5-30% by weight. In an alternative embodiment, the pH is 8.0-11-3. In still a further embodiment, the process is performed as a batch process, or, alternatively, as a continuous process. In still another embodiment, the average copper dissolution rate is about 17 g/l-hour.

The invention will be further understood by the following non-limiting examples.

EXAMPLES

Example 1

Impact of Geometric Surface

To illustrate impact of geometric surface, two batches of copper monoethanolamine solution were prepared using #1 fine and #1 heavy and the rates of dissolution determined. A 2-liter Parr reactor fitted with double blade agitator, air/gas inlet tube, gas vent to atmosphere, cooling cools and heating jacket. A microprocessor-controlled unit maintained the temperature by turning off the heating jacket and passing tap water thorough the cooling coils.

The reaction mixtures included 635 grams of monoethanolamine, 532 grams of water, 124 grams of carbon dioxide (1.08:1 $CO_2$:Cu) and 330 grams of metallic copper, which is about twice the copper required to form a 1:4 copper:ethanolamine complex. Air was passed through the mixtures such that the rate would provide an adequate amount of oxygen after 12 hours of airflow, e.g., to produce copper in ethanolamine where the ratio of copper to ethanolamine is 1:4. The reaction mixture was heated to 65° C. and maintained at that temperature throughout the copper dissolution. The following table (Table 1) illustrates the impact of copper geometric surface on the initial rate of copper dissolution for the #1 fine and heavy copper samples.

TABLE 1

Impact of Copper Geometric Surface

| Reaction Time At | Percent Copper Dissolved | |
|---|---|---|
| 65° C. | #1 Fine | #1 Heavy |
| 1 | 0.18 | 0.14 |
| 2 | 0.66 | 0.28 |
| 3 | 1.60 | 1.10 |
| 4 | 3.86 | 2.65 |
| 5 | 6.27 | 5.03 |
| 6 | 8.50 | 7.44 |

This reaction is heterogeneous and the reaction conditions are such that the copper surface impacts the rate of copper dissolution. The overall amount of copper in solution is unexpected, and shows improved results.

Example 2

Impact of Temperature on Dissolution of Copper

It is preferable that the dissolution of copper proceed as rapidly as possible with little or no oxidation of the monoethanolamine by the copper (II) or cupric ion. This oxidation reaction is both time and temperature dependent. The conditions can be optimized to avoid oxidation of alkyl hydroxylamine, which can occur above 110° C.

To determine the impact of temperature on the oxygen dissolution of copper in aqueous ethanolamine solutions containing carbon dioxide, four reactions were conducted. Temperatures for the oxygen dissolution of copper were selected to reduce observable oxidation of ethanolamine and generation of copper (I) or cuprous. The four temperatures selected were 45, 55, 65 and 75° C. The reactants used and reaction conditions were as described in Example 1, except only #1 heavy copper metal was used as the source of the copper. The impact of temperature on the initial rate of copper dissolution in the ethanolamine/water/carbon dioxide mix is shown in Table 2.

TABLE 2

| | Temperature versus Copper Dissolution | | | |
|---|---|---|---|---|
| Time, | Percent Copper Dissolved | | | |
| hrs. | 45° C. | 55° C. | 65° C. | 75° C. |
| 2 | 0.12 | 0.19 | 0.28 | 0.90 |
| 4 | 0.31 | 0.94 | 2.65 | 5.58 |
| 6 | 0.96 | 3.07 | 7.44 | 8.92 |

Example 3

Concentration of Ethanolamine

The concentration on the ethanolamine can have impact on the reaction kinetics or rate of copper dissolution. This may be due to a variety of factors, such as oxygen solubility, solution viscosity, solubility of product in aqueous mixture, etc. To test the impact, experiments were done with a reduced amount of water available in the reaction vessel and the initial rate of copper dissolution examined.

The reaction mixture was identical to that in Example 1, except that only half the water was added to the reactor. To maintain the same volume element in the reactor, the solution/copper metal content was increased appropriately. Thus, the reaction mixture included 759 grams of monoethanolamine, 327 grams of water, 126 grams of carbon dioxide and 395 grams of metallic copper. The reactor process conditions were as described in Example 1. The rate results of these experiments are provided in Table 3.

TABLE 3

Ethanolamine Concentration versus Copper Dissolution

| Time, hrs. | Control | Half Water as Control |
| --- | --- | --- |
| 2 | 0.28 | 0.25 |
| 4 | 2.65 | 1.28 |
| 6 | 7.44 | 4.50 |
| 8 | 9.15 | 7.76 |

These results indicate that the concentration of ethanolamine in the reaction mixture can have an impact on the initial rate of copper dissolution.

Example 4

Impact of Carbon Dioxide on Reaction Kinetics

In a specific embodiment, carbon dioxide, an acid anhydride, is added to the ethanolamine-water mixture to generate the protonated ethanolamine carbonate salt. Since air is sparged through the heated mixture of ethanolamine, water, carbon dioxide and metallic copper, carbon dioxide can be flushed from the reaction mixture such that an insufficient amount remains to dissolve the desired amount of copper. The above examples contained a slight excess of carbon dioxide to copper (1.08:1 mole ratio) and about twice the amount of copper required to form the 1:4 copper:ethanolamine mole ratio complex. Experiments were conducted to determine the impact of a stiochiometric amount of carbon dioxide and a large excess of carbon dioxide. These were compared to the controls as described in Examples 1-3.

The examination of carbon dioxide impact on the reaction kinetics was tested at 8.9 (0.98:1 mole ratio) and 12.0 (1.36:1 mole ratio) percent by weight dissolved carbon dioxide in aqueous ethanolamine and compared to the control of 9.6 percent (1.08:1 mole ratio), which was used in the previous examples. The reaction amounts and conditions were as described in Example 1. The results for these experiments are shown in FIG. 1, which shows that the stiochiometric amount of carbon dioxide give initial rates of reaction greater that those for both the 9.6 and 12.0 percent by weight carbon dioxide reaction mixtures. However, the results also indicate that both the 8.9 and 9.6 eventually yield the same overall total contained copper in solution. The reaction time will differ depending on the amount of $CO_2$ present.

Example 5

Ratio of Copper to Ethanolamine

Water insoluble salts of copper such as copper hydroxide, copper carbonate and basic copper carbonate can be dissolved in aqueous ethanolamine solutions to give mole ratios less than 4. The lower the mole ratio of copper to ethanolamine, the lower the cost of the copper ethanolamine solution and thus the overall wood preservative costs. Typically, mole ratios of about 1:3.5 copper to ethanolamine are ideal for wood preservation formulations. Lower than this value gives rise to potential loss of copper by precipitation from the aqueous commercial wood treating solutions. Normally, the chemistry is such that one carbonate ion and four ethanolamine molecules are required per copper atom, and, assuming this to be the case, reactions at the standard Example 1 conditions should give rise to a final or predicted solution copper concentration of 11.1 percent. However, to test if further copper dissolution could occur all reactions were continued past the 11.1 percent dissolved copper.

Figure 2:
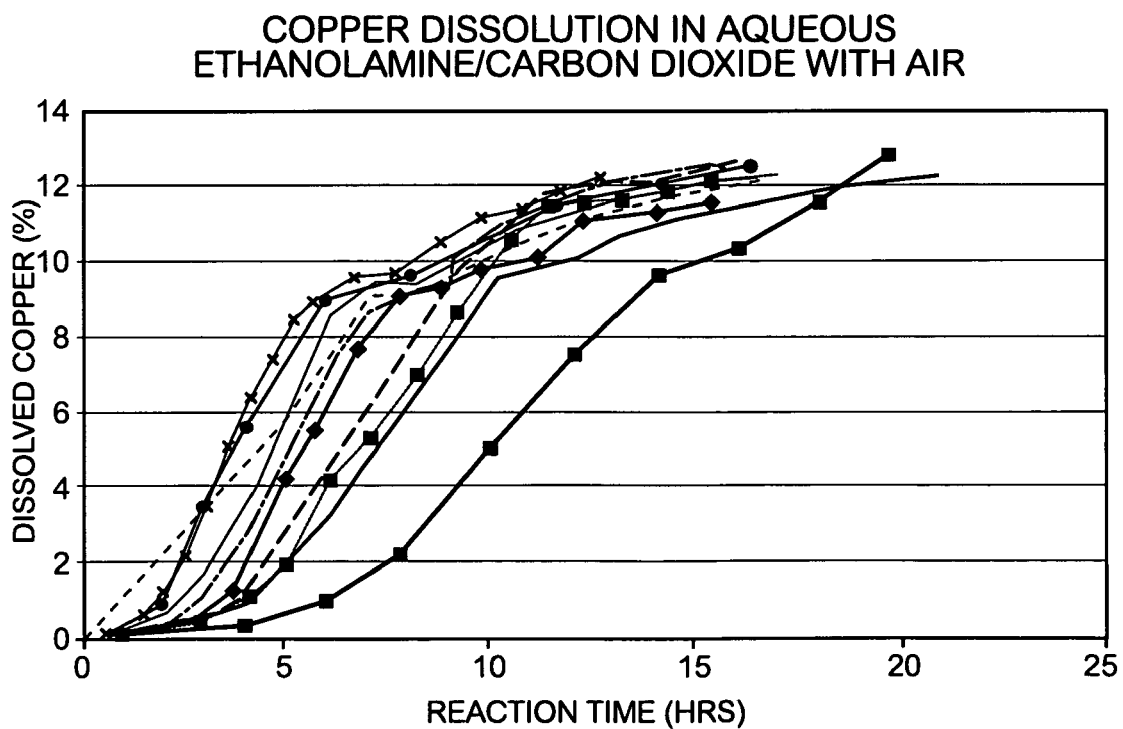
FIG. 2 is a graph of various reactions of copper dissolution in aqueous monoethanolamine/carbon dioxide solution with air.

Reactions were run using many of the reactant quantities and process conditions described in Examples 1-3, e.g. various copper sources/purities/surface, ethanolamine concentrations and reaction temperatures. The reactions were permitted to continue past the 1:4 copper to ethanolamine mole ratio. The results of these experiments are shown in FIG. 2. The unexpected result in all cases was that the dissolved copper increased past the 11.1 percent assay, or the 1:4 copper:ethanolamine ratio to approach or reach the mole ratio of 1:3.5 at a dissolved copper of 12.3 percent.

Example 6

Effect of Pressure

To examine if increasing the air pressure or oxygen partial pressure would have an impact on the reaction rates, experiments were conducted at both 65 and 85° C. with increased air pressure.

Figure 3:
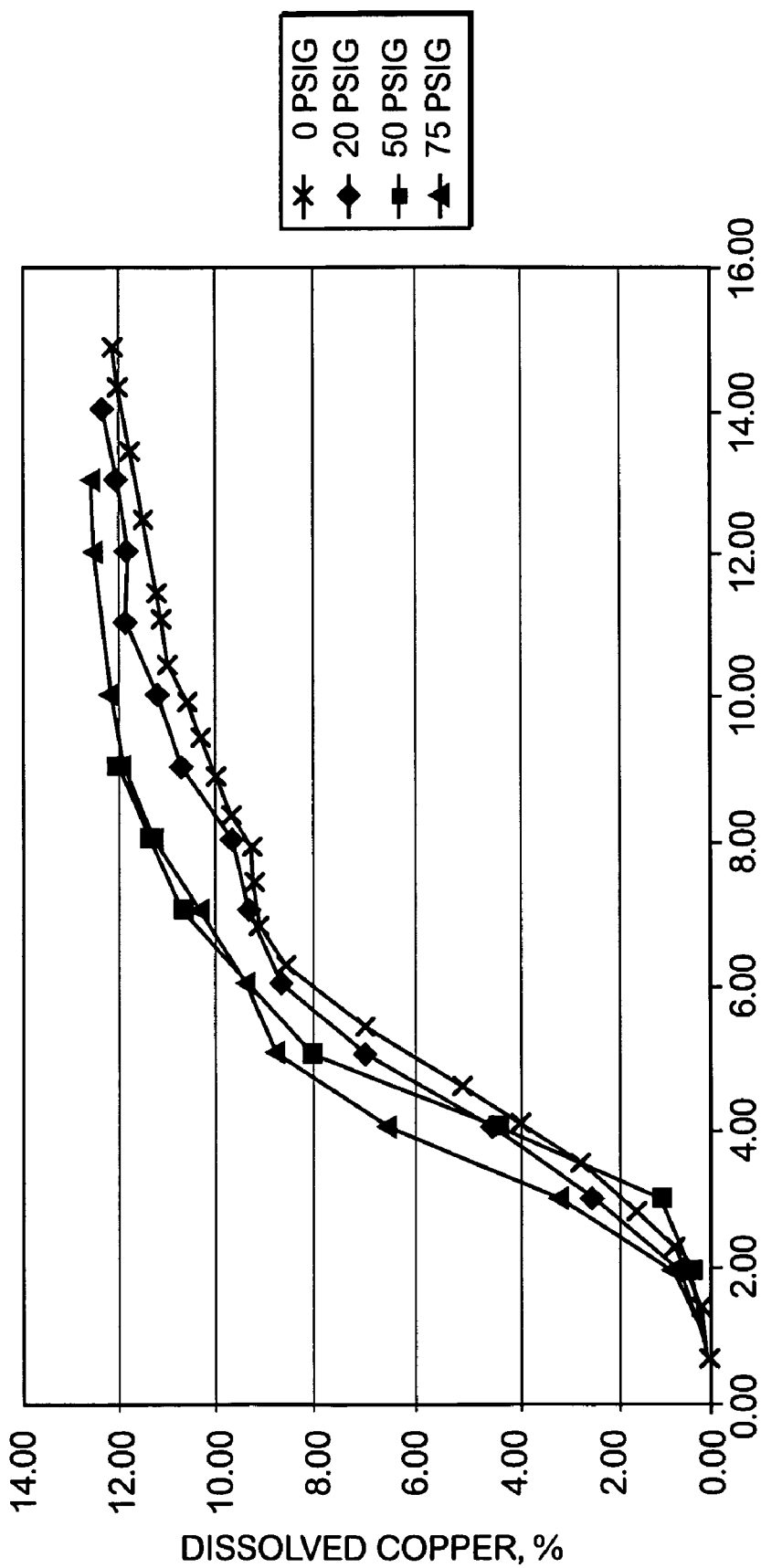
FIG. 3 is a graph showing the effect of increased air pressure on copper dissolution in the presence of monoethanolamine at 65° C.
Figure 4:
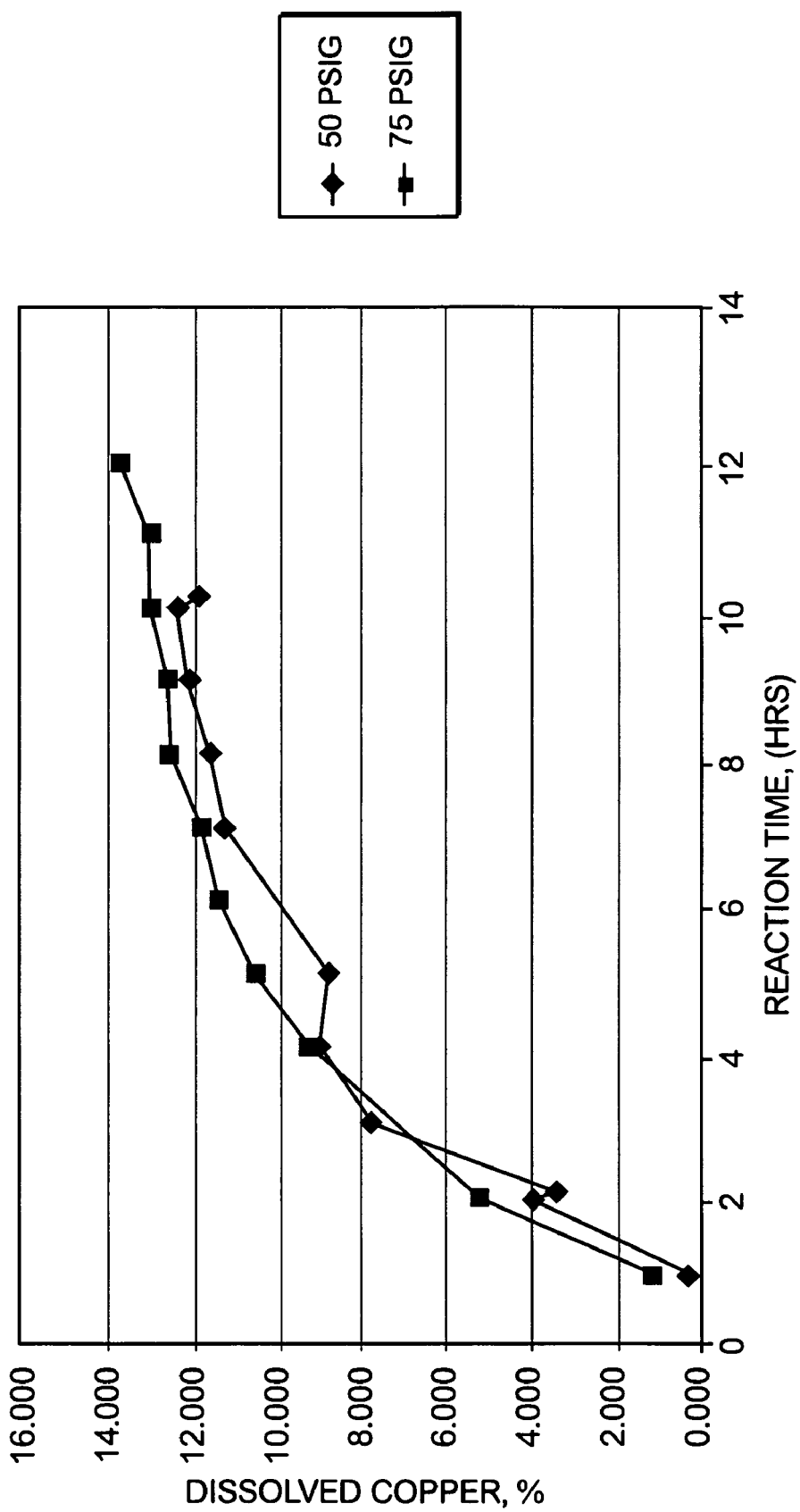
FIG. 4 is a graph showing the effect of increased air pressure on copper dissolution in the presence of monoethanolamine at 85° C.

The reactions used 663 grams of monoethanolamine, 555 grams of water and 118 grams of dissolved carbon dioxide. Into this reaction mixture, 330 grams of copper metal (heavy #1) were added. The air pressures were adjusted to 20, 50 and 75 psig for each experiment. The results are shown in FIGS. 3 and 4, for 65 and 85° C. temperature runs. Increasing the partial pressure of oxygen drastically increases the reaction rates, such that reactions can be completed in 5 hours or less, a significant improvement compared to reported copper dissolution reactions in ethanolamine solutions.

Example 7

Apparatus

A variety of reactor designs can be used. The reactor systems for producing copper ethanolamine aqueous solutions can include, e.g., reaction vessels, stirrers, gas sources, inlet and outlet valves, pressurized systems, inlet and outlet lines, thermocouples, heaters, agitators, gas diffusers, tanks, pumps, cooling jackets, scrubbers, steam sources, etc. The reactor systems described herein can be used in any of the reactions described herein, and the discussion of systems for the production of copper ethanolamine aqueous solutions is provided by way of example.

Figure 5:
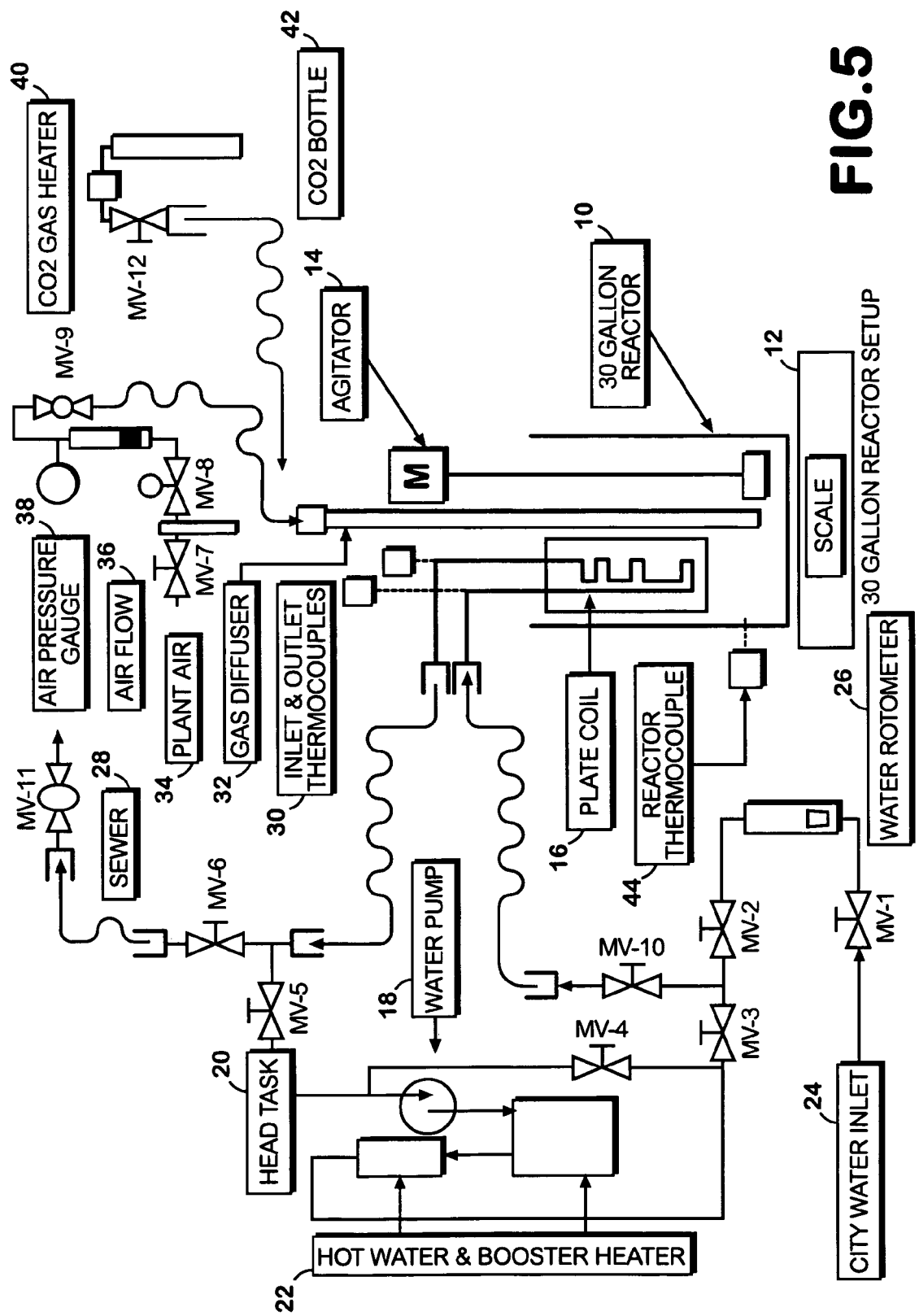
FIG. 5 is an illustration of reactor system including 30 gallon reactor for the preparation of copper monoethanolamine aqueous solutions with reaction at atmospheric pressure.

On embodiment of a reactor system is a 30 gallon reactor, in which, for example, the reaction can be conducted at atmospheric pressure, as shown in FIG. 5. As shown in FIG. 5, the 30 gallon reactor system includes a reactor 10 upon scale 12, agitator 14 and plate coil 16. The system includes water pump 18 that includes hot water heater and booster heaters 22, head tank 20, city water inlet 24, water rotameter 26, and sewer outlet 28. The system further includes inlet and outlet thermocouples 30, gas diffuser 32, plant air source 34, air flow conduit 36, air pressure gauge 38, and $CO_2$ gas heater 40 as well as $CO_2$ bottle 42 and reactor thermocouple 44. Thus, during operation, reactants are delivered to the 30 gallon reactor and can be measured using the scale. The solution can be heated using the plate coil, and stirred with the agitator. Gases can be delivered to the solution using the gas diffuser.

Figure 6:
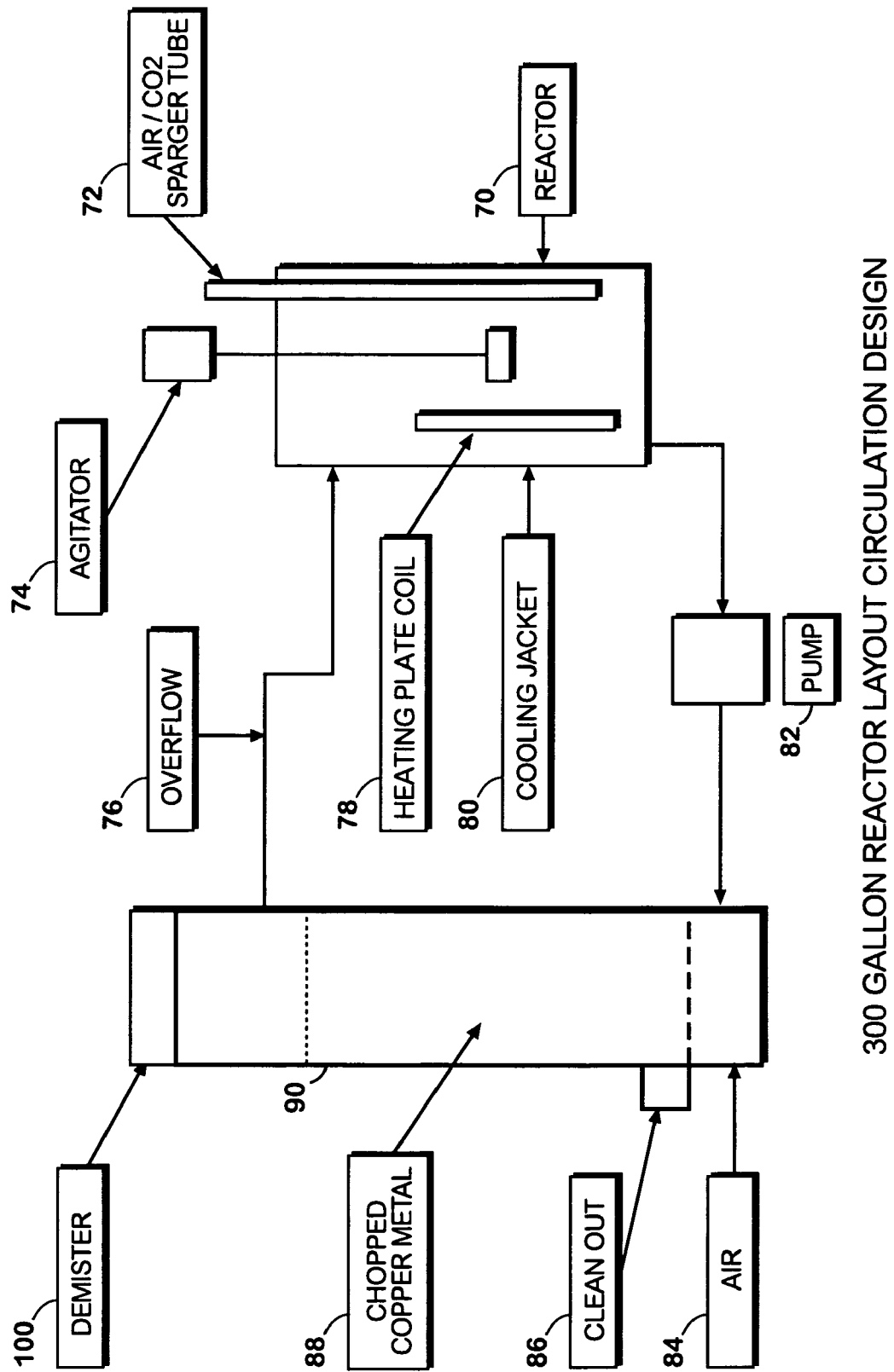
FIG. 6 is an illustration of a 300 gallon reactor system with a pump through column design for the preparation of copper monoethanolamine aqueous solutions.

Another embodiment of a reactor system is shown in FIG. 6, which includes a reactor 70, air/$CO_2$ sparger tube 72, agitator 74, heating plate coil 78, cooling jacket 80, pump 82, air source 84, clean out 86, chopped copper metal 88, column 88 and demister 90. This system permits copper metal to be provided in a column or tube 90, with e.g. a metal filter mesh supporting the copper in the tube. The water and ethanolamine are provided in the reactor 70, and the air and $CO_2$ are inserted using the sparger tube 72 and mixed with the agitator 74. The solution is heated with the heating plate coil and passed via the pump 82 upward through the copper filled column 90 to react with the copper. This is an efficient method and can improve the yield and reaction time. For example, the reaction time may be less than 5, 6, 7, 8 or 9 hours. The liquid can be recirculated through the column.

Figure 7:
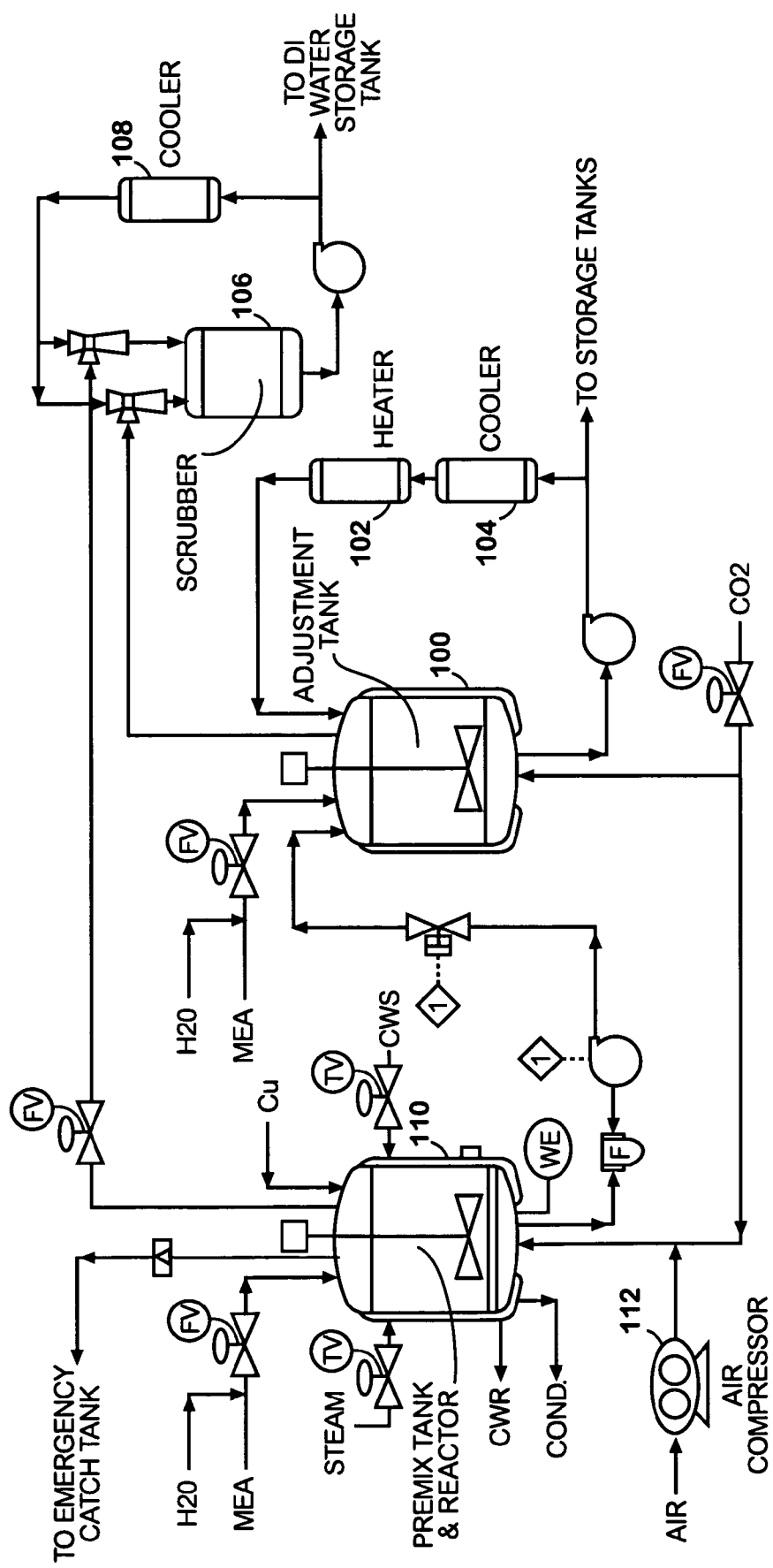
FIG. 7 is an illustration of a layout of a pressure reactor design for a reactor system for the preparation of copper monoethanolamine aqueous solutions.

A layout of a pressure reactor design is shown in FIG. 7. In the system, water, $CO_2$ and ethanolamine (MEA) may be charged to a premix tank and reactor 110 which contains copper metal. Pressurized air is pumped through the copper metal/solvent blend and the copper dissolves. When completed the solution is pumped to adjustment tank 100 where the balance of the $CO_2$ and water is added. The system further includes air compressor 112, cooler 104, heater 102, scrubber 106 and cooler 108.

In the apparatus of FIG. 7, a second option is to have a premix reactor containing the MEA, $CO_2$ and water. This premix is pumped, under pressure, through copper metal that is contained in a second reactor that may not be agitated.

Figure 12:
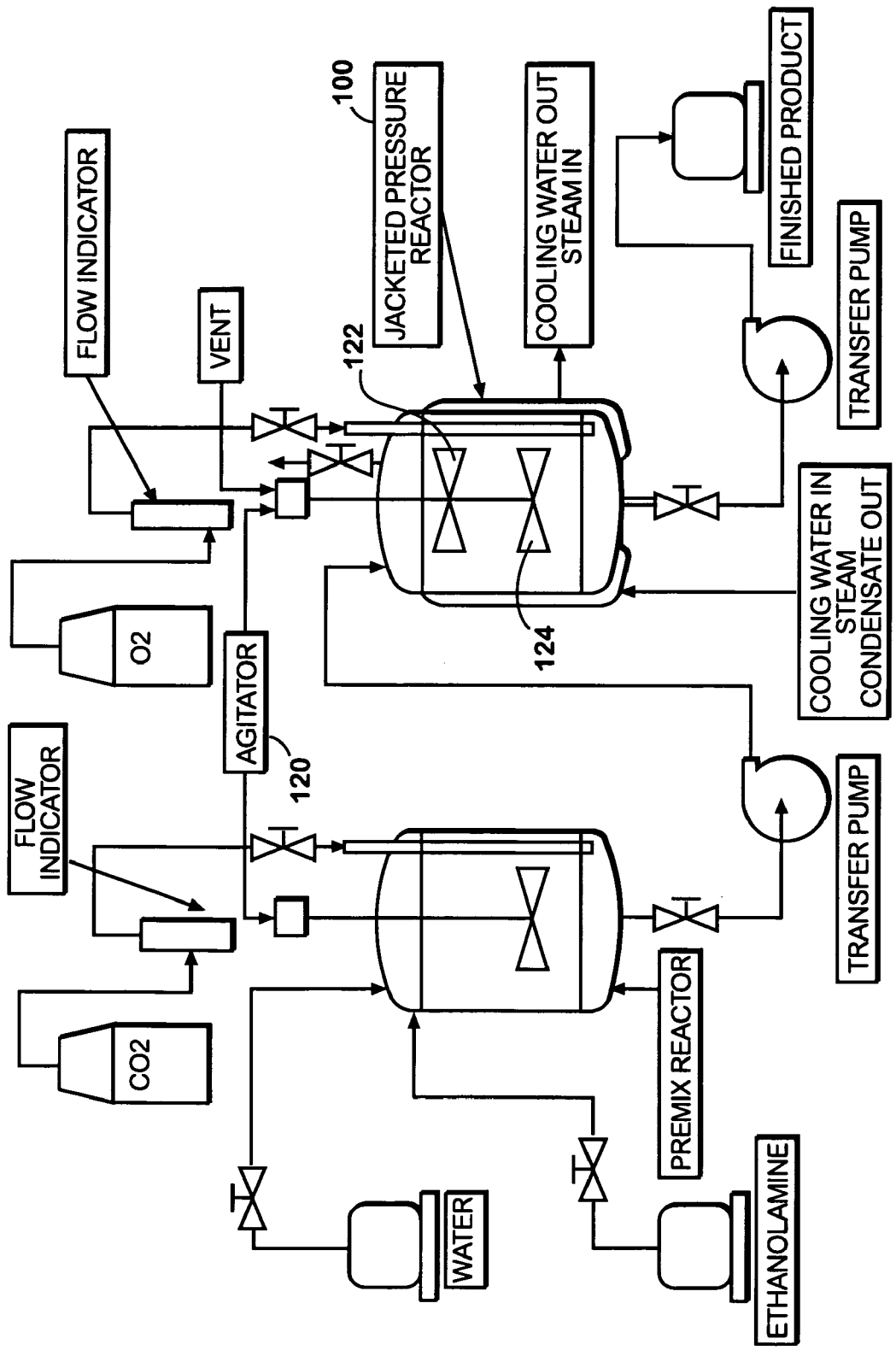
FIG. 12 is an illustration of a layout of a pressure reactor design for a reactor system for the preparation of copper ethanolamine aqueous solutions, wherein the agitator contains both a propeller for stirring solid copper material and a propeller for dispersing liquid into the atmosphere above the liquid in the tank.

Another embodiment is shown in FIG. 12, which shows that agitator 120 includes a propeller 124 for stirring solid copper material and a propeller 122 for dispersing liquid into the atmosphere above the liquid in tank 100.

Example 8

Scale Up of Reaction

Experiments similar to those described above were conducted in a 30-gallon reactor to scale up the reaction.

An insulated 30-gallon stainless steel reactor equipped with an agitator was used during the process. Heating and cooling of the reactor was done using a hot water heater and city water, respectively. The heating and cooling were supplied to a stainless steel hot plate located in the reactor. Oxygen and $CO_2$ gas were added through a Mott sparger. Oxygen was supplied from compressed plant air and carbon dioxide from a commercial dewar. Supplemental ventilation and exhaust fans were used to aid in the removal of any MEA vapors produced in the reaction.

Figure 8:
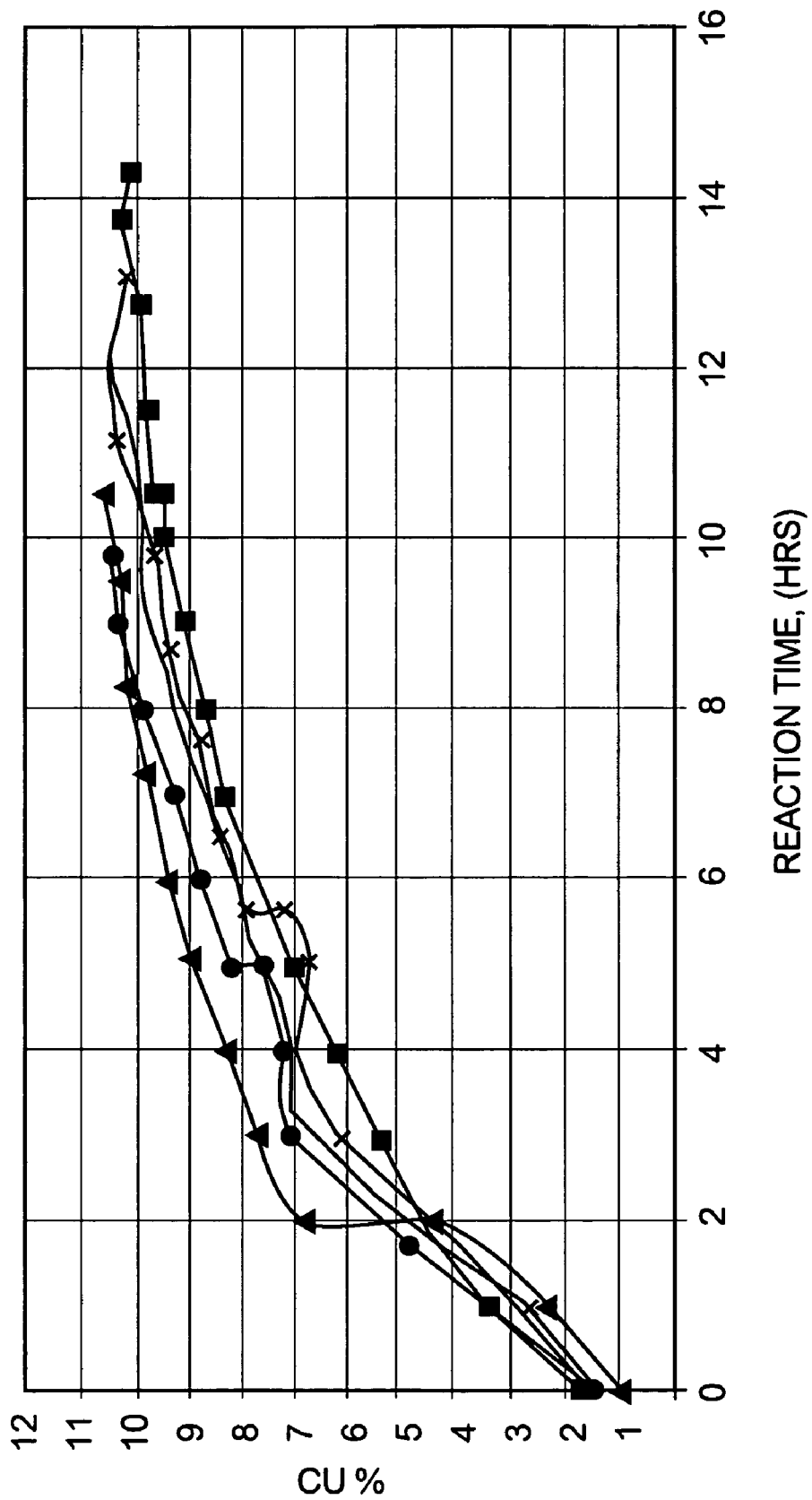
FIG. 8 is a graph of showing dissolution of copper in monoethanolamine aqueous solution versus reaction time.

Various conditions were changed throughout the batches to determine their impact on the reaction rate. The results of these experiments are shown in FIG. 8. Reaction times of 10-14 hours were typical for a 10-10.5% copper solution.

Example 9

Scale-up Using a 300 Gallon/Column Reactor

In one embodiment, a 300 gallon column reactor is used, for example, with air at atmospheric conditions, or under pressure, e.g. 50 or 75 psig. The reaction, e.g., takes about 12-13 hours per batch, and optionally a heel can be used. Other embodiments of reactor size and pressure are possible, such as a 50 gallon reactor with 50 psig oxygen.

Figure 9:
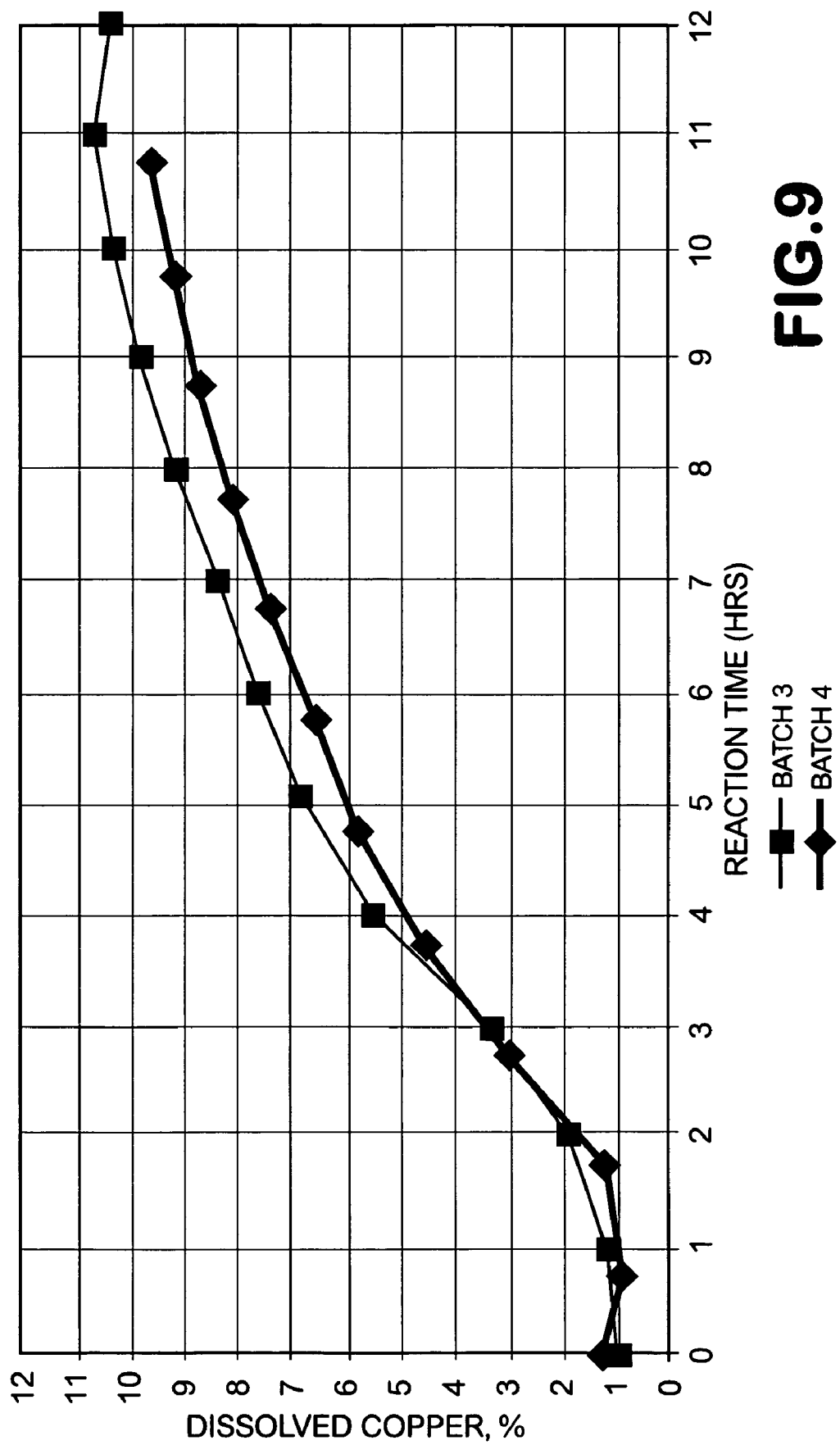
FIG. 9 is a graph of dissolved copper concentration vs reaction time for a reaction in a 300 gallon reactor.

The column (90) as shown in FIG. 7, was charged with some 280 pounds of chopped, #1 scrap copper. Some 670 lbs. of water were charged to the 300-gallon reactor (70), followed by the addition of 465 lbs. of monoethanolamine. To this solution, some 75 lbs. of carbon dioxide was added through a sparger tube (72) from a liquid carbon dioxide commercial Dewar. Solution weights were monitored via a weigh scale placed under the 300-gallon reactor. The solution was heated to approximately 80-85° C. by a heating plate coil (78) and air was sparged into the solution (5.7 scfm in reactor/2 scfm in bottom of column), which solution was subsequently pumped (82) through the column containing the copper metal (88) at a flow rate of (15-20 gpm). The solution flow exiting the column (90) was recycled back into the 300-gallon reactor. Samples were removed periodically and dissolved copper measured. The results of two experiments using this apparatus are shown in FIG. 9. Under the parameters used for these two experiments, it appears that the reaction time required to produce 10.2-10.3 percent copper in solution is in the range of 12-14 hours. An increase in the solution flow rate through the column, optionally coupled with increased air sparge rate at both the reactor and the column could reduce this reaction time considerably.

Example 10

Reaction with Oxygen

The reactions can use air for the source of oxygen, or pure oxygen. Pure oxygen is available commercially in liquid and gas form. Increasing the pressure of air in the reactor can dramatically improve the rate of copper dissolution to form copper ethanolamine. The increase in air pressure impacts the solubility of oxygen (and probably nitrogen) in the reaction matrix, thus improving the overall rate of copper dissolution. Oxygen availability can be increased further, by using pure oxygen instead of air. Although pure oxygen could pose a potential fire/explosion hazard with ethanaolamine in aqueous solutions, the oxygen pressure can be adjusted so that no oxygen-ethanolamine reactions occur.

Figure 10:
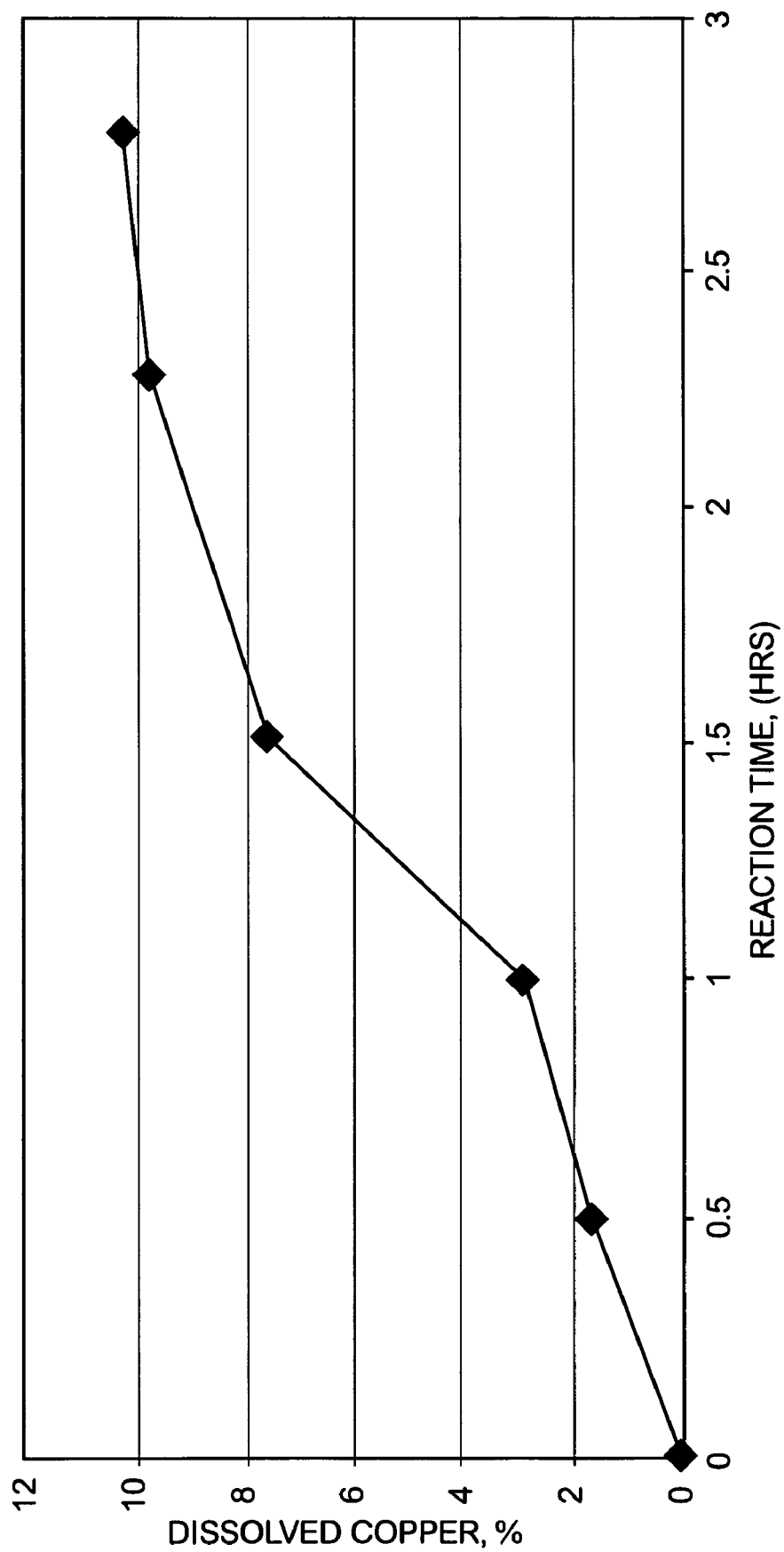
FIG. 10 is a graph of dissolved copper concentration vs. reaction time demonstrating the impact of pure oxygen on copper dissolution in monoethanolamine/ carbon dioxide solutions at 85° C., with oxygen at 25 psig.

To determine the impact of oxygen on the dissolution rate, a reaction was done using the Parr reactor described in Example 1. The reactor was charged with 306 grams of #1 heavy copper, 515 grams of ethanolamine, 709 grams of water and 85 grams of carbon dioxide (0.8:1.00 $CO_2$:Cu). Oxygen was added to the reactor and maintained at 25 psig throughout the course of the reaction. The temperature of the reactor was maintained at 85° C. FIG. 10 shows the impact of pure oxygen on copper dissolution in ethanolamine/carbon dioxide solutions at 85° C. with oxygen at 25 psig. As shown in FIG. 10, the reaction generated 10.22 percent copper ethanolamine in about 2.75 hours. This dramatic rate of copper dissolution is valuable and efficient.

Example 11

Reaction with Oxygen—Batch Reaction

To further evaluate the impact of oxygen on the dissolution rate, reactions were conducted using a 50 gallon reactor setup similar to that described in Example 7 except that pure oxygen was used in the place of air. The reactor was charged with approximately 50# of copper metal scrap and a stock solution containing about 172 pounds of monoethanolamine, 34 pounds of carbon dioxide, and 224 pounds of water.

Figure 11:
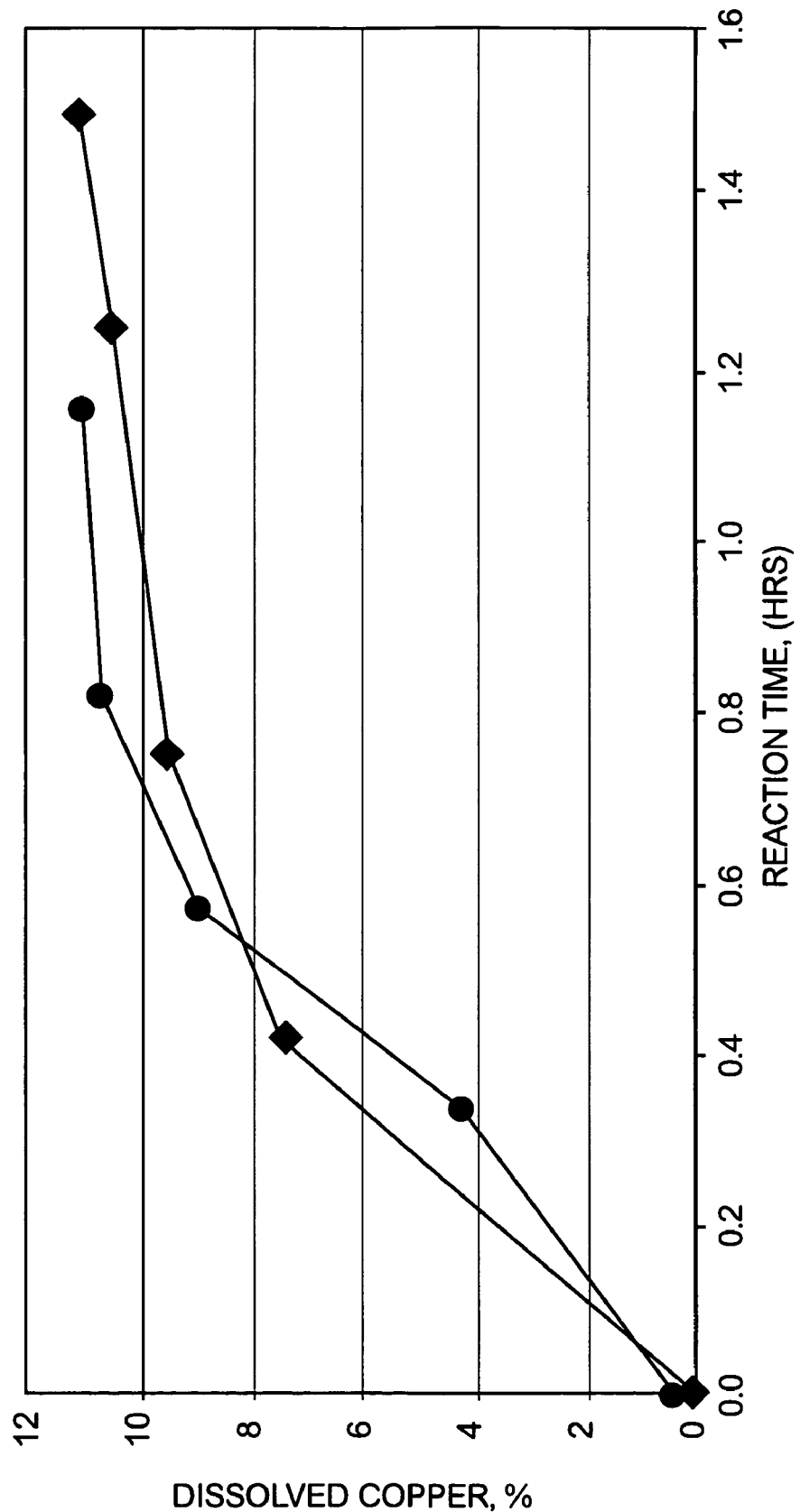
FIG. 11 is a graph of the impact of pure oxygen on copper dissolution in monoethanolamine/carbon dioxide solutions in a 50 gallon reactor at 75° C., and oxygen at 30 psig.

Oxygen was added to the reactor and maintained between 25 psig & 30 psig throughout the course of the reaction. The temperature of the reactor was maintained at 75° C. FIG. 11 shows the impact of pure oxygen on copper dissolution in ethanolamine/carbon dioxide solutions at 75° C. with oxygen at 30 psig. As shown in FIG. 11, the reactions generated between 10.99 and 11.15 percent copper ethanolamine in between 1.15 & 1.5 hours. Reaction rates ranged between 94 and 120 grams of copper per liter per hour. This dramatic rate of copper dissolution is valuable and efficient.

Modification and variations of the present invention would be obvious to those skilled in the art from the above descriptions of the invention, and such variations are intended to fall under the scope of the following claims.

What is claimed is:

1. A method for producing an aqueous copper monoethanolamine solution product comprising:
    a) charging to a reaction vessel water, monoethanolmine, and a metallic copper bearing material to a reaction vessel, pumping pressurized air at a pressure of 20 to 90 psig through the vessel to provide a mixture, pumping the mixture to a second vessel where $CO_2$ and water are added,
    b) maintaining the temperature in the second vessel at from about 40° C. to 115° C. to dissolve the metallic copper to provide a copper monoethanolamine solution; and
    c) optionally removing excess metallic copper or other extraneous solids from the dissolved copper monoethanolmine solution,
    thereby to form the copper monoethanolamine solution product.

2. The method of claim 1, wherein the temperature is about 65-85° C.

3. The method of claim 1, wherein the temperature is about 70-115° C.

4. The method of claim 1, wherein the molar ratio of carbon dioxide to dissolved copper in the product is about 0.5 to 1.5.

5. The method of claim 1, wherein the mole ratio of carbon dioxide to dissolved copper in the product is about 0.7-0.8.

6. The method of claim 1, wherein the molar ratio of monoethanolamine to dissolved copper in the product is about 2.5 to 4.

7. The method in claim 1, wherein the mole ratio of monoethanolamine to dissolved copper in the product is 3.5-4.0.

8. The method of claim 1, wherein the dissolved copper concentration in the product is approximately 8-15 weight percent.

9. The method of claim 1, wherein the dissolved copper concentration in the product is approximately 10-15 weight percent.

10. The method of claim 1, wherein the metallic copper bearing material is ultrapure, #1 scrap or #2 scrap and is optionally bulk or chopped.

11. The method of claim 1, wherein the reaction vessel of step a) is a stirred tank open to the atmosphere.

12. The method of claim 1, wherein the reaction vessel in at least one of steps a), b) and c) is under pressure.

13. The method of claim 1, wherein in step b) the mixture is maintained at a temperature of about 90-115° C.

14. A method for producing an aqueous copper monoethanolamine solution product comprising:
    a) charging to a reaction vessel water, monoethanolamine, and a metallic copper bearing material to a reaction vessel, pumping pure oxygen at a pressure of 20 to 90 psig through the vessel to provide a mixture, pumping the mixture to a second vessel where $CO_2$ and water are added,
    b) maintaining the temperature in the second vessel at from about 40° C. to 115° C. to dissolve the metallic copper to provide a copper monoethanolamine solution; and
    c) optionally removing excess metallic copper or other extraneous solids from the dissolved copper monoethanolamine solution,
    thereby to form the copper monoethanolamine solution product.

15. The method of claim 14, wherein the pressure of the oxygen introduced into the vessel is from 30 to 50 psig.

16. The method of claim 14, wherein the pressure of the oxygen introduced into the vessel is from 20 to 40 psig.

* * * * *